United States Patent
Nye et al.

(10) Patent No.: US 10,811,135 B2
(45) Date of Patent: Oct. 20, 2020

(54) SYSTEMS AND METHODS TO DETERMINE DISEASE PROGRESSION FROM ARTIFICIAL INTELLIGENCE DETECTION OUTPUT

(71) Applicant: General Electric Company, Schenectady, NY (US)

(72) Inventors: Katelyn Nye, Waukesha, WI (US); Gireesha Rao, Waukesha, WI (US); Gopal Avinash, San Ramon, CA (US); Christopher Austin, Seattle, WA (US)

(73) Assignee: General Electric Company, Schenectady, NY (US)

( * ) Notice: Subject to any disclaimer, the term of this patent is extended or adjusted under 35 U.S.C. 154(b) by 102 days.

(21) Appl. No.: 16/233,670

(22) Filed: Dec. 27, 2018

(65) Prior Publication Data

US 2020/0211694 A1    Jul. 2, 2020

(51) Int. Cl.
| | |
|---|---|
| *G06T 7/00* | (2017.01) |
| *G16H 30/40* | (2018.01) |
| *G06T 7/11* | (2017.01) |
| *G16H 50/20* | (2018.01) |

(52) U.S. Cl.
CPC ........... *G16H 30/40* (2018.01); *G06T 7/0016* (2013.01); *G06T 7/11* (2017.01); *G16H 50/20* (2018.01)

(58) Field of Classification Search
CPC ...... G16H 30/40; G16H 50/20; G06T 7/0016; G06T 7/11; G06T 7/0012;
(Continued)

(56) References Cited

U.S. PATENT DOCUMENTS

| | | | | |
|---|---|---|---|---|
| 6,366,797 | B1 * | 4/2002 | Fisher | A61B 5/055 128/922 |
| 7,970,188 | B2 * | 6/2011 | Mahesh | G06Q 50/22 382/128 |
| 2007/0081707 | A1 * | 4/2007 | Sirohey | G06F 19/00 382/128 |
| 2007/0230763 | A1 * | 10/2007 | Matsumoto | G06T 7/0012 382/131 |

(Continued)

OTHER PUBLICATIONS

Salazar et al., "Evaluation of Three Pneumothorax Size Quantification Methods on Digitized Chest X-ray Films Using Medical-Grade Grayscale and Consumer-Grade Color Displays," published on Oct. 23, 2013, 13 pages.

(Continued)

*Primary Examiner* — Carol Wang
(74) *Attorney, Agent, or Firm* — Hanley, Flight and Zimmerman, LLC

(57) ABSTRACT

Apparatus, systems, and methods to improve automated identification, monitoring, processing, and control of a condition impacting a patient using image data and artificial intelligence classification are disclosed. An example image processing apparatus includes an artificial intelligence classifier to: process first image data for a patient from a first time to determine a first classification result indicating a first severity of a condition for the patient; and process second image data for the patient from a second time to determine a second classification result indicating a second severity of the condition for the patient. The example image processing apparatus includes a comparator to compare the first classification result and the second classification result to determine a change and a progression of the condition associated with the change. The example image processing apparatus includes an output generator to trigger an action when the progression corresponds to a worsening of the condition.

16 Claims, 17 Drawing Sheets

(58) Field of Classification Search
CPC . G06T 2207/30096; G06T 2207/10132; G06T 2207/10116; G06T 2207/10081; G06T 2207/30061; G06T 2207/30088; G06T 2207/10072; G06T 2207/10076; G06T 2207/10088; G06T 2207/10101; G06T 2207/10104; G06T 2207/30008; G06T 2207/30012; G06T 2207/30028; G06T 2207/30041; G06T 2207/30081; G06T 2207/30101; A61B 6/50; A61B 2576/00; A61B 5/0013; A61B 5/7267; A61B 5/7264; A61B 5/4088; A61B 5/412; A61B 5/4842

See application file for complete search history.

(56) References Cited

U.S. PATENT DOCUMENTS

| | | | |
|---|---|---|---|
| 2017/0091930 A1* | 3/2017 | Kozuka | G06F 16/50 |
| 2018/0113984 A1* | 4/2018 | Doshi | G16H 50/20 |
| 2018/0122068 A1* | 5/2018 | Garnavi | G06K 9/6274 |
| 2018/0289336 A1 | 10/2018 | Osawa | |
| 2019/0189268 A1* | 6/2019 | Stoval, III | G16H 50/20 |

OTHER PUBLICATIONS

Carestream, "Carestream's companion-view processing for improved visualization of tubes, lines, and pneumothoraces in digital, portable chest radiography", www.carestream.com, 2012, 4 pages.

European application 19219569.1 filed Dec. 23, 2019—Search Report dated May 28, 2020, 8 pages.

\* cited by examiner

SYSTEMS AND METHODS TO DETERMINE DISEASE PROGRESSION FROM ARTIFICIAL INTELLIGENCE DETECTION OUTPUT

FIELD OF THE DISCLOSURE

This disclosure relates generally to improved medical systems and, more particularly, to improved learning systems and methods for medical image processing.

BACKGROUND

A variety of economy, operational, technological, and administrative hurdles challenge healthcare facilities, such as hospitals, clinics, doctors' offices, imaging centers, teleradiology, etc., to provide quality care to patients. Economic drivers, less skilled staff, fewer staff, complicated equipment, and emerging accreditation for controlling and standardizing radiation exposure dose usage across a healthcare enterprise create difficulties for effective management and use of imaging and information systems for examination, diagnosis, and treatment of patients.

Healthcare provider consolidations create geographically distributed hospital networks in which physical contact with systems is too costly. At the same time, referring physicians want more direct access to supporting data in reports along with better channels for collaboration. Physicians have more patients, less time, and are inundated with huge amounts of data, and they are eager for assistance.

Healthcare provider (e.g., x-ray technologist, doctor, nurse, etc.) tasks including radiological image acquisition, quality assurance/quality control, image interpretation, image comparison to priors, etc., are time consuming and resource intensive tasks impractical, if not impossible, for humans to accomplish alone.

BRIEF SUMMARY

Certain examples provide apparatus, systems, and methods to improve automated identification, monitoring, processing, and control of a condition impacting a patient using image data and artificial intelligence classification.

Certain examples provide an image processing apparatus including an artificial intelligence classifier to: process first image data for a patient from a first time to determine a first classification result indicating a first severity of a condition for the patient; and process second image data for the patient from a second time to determine a second classification result indicating a second severity of the condition for the patient. The example image processing apparatus includes a comparator to compare the first classification result and the second classification result to determine a change and a progression of the condition associated with the change. The example image processing apparatus includes an output generator to trigger an action when the progression corresponds to a worsening of the condition.

Certain examples provide at least one computer-readable storage medium including instructions. The instructions, when executed, cause at least one processor to at least: process first image data for a patient from a first time to determine a first classification result indicating a first severity of a condition for the patient; process second image data for the patient from a second time to determine a second classification result indicating a second severity of the condition for the patient; compare the first classification result and the second classification result to determine a change and a progression of the condition associated with the change; and trigger an action when the progression corresponds to a worsening of the condition.

Certain examples provide a computer-implemented method including processing, by executing an instruction using at least one processor, first image data for a patient from a first time to determine a first classification result indicating a first severity of a condition for the patient. The example method includes processing, by executing an instruction using at least one processor, second image data for the patient from a second time to determine a second classification result indicating a second severity of the condition for the patient. The example method includes comparing, by executing an instruction using at least one processor, the first classification result and the second classification result to determine a change and a progression of the condition associated with the change. The example method includes triggering, by executing an instruction using at least one processor, an action when the progression corresponds to a worsening of the condition.

Figure 1:
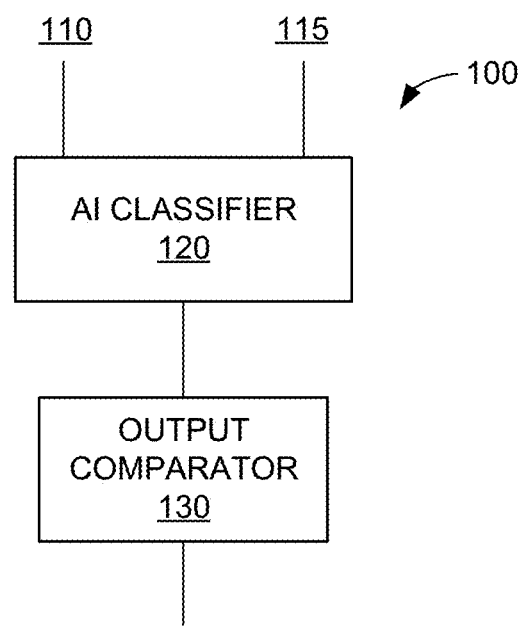
FIG. 1 illustrates an example condition comparator.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings. The figures are not scale. Wherever possible, the same reference numbers will be used throughout the drawings and accompanying written description to refer to the same or like parts.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

While certain examples are described below in the context of medical or healthcare systems, other examples can be implemented outside the medical environment. For example, certain examples can be applied to non-medical imaging such as non-destructive testing, explosive detection, etc.

I. Overview

Imaging devices (e.g., gamma camera, positron emission tomography (PET) scanner, computed tomography (CT) scanner, X-Ray machine, fluoroscopy machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, quality control, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine and/or deep learning can be used to help configure, monitor, and update the medical imaging workflow and devices.

Certain examples provide and/or facilitate improved imaging devices which improve diagnostic accuracy and/or coverage. Certain examples facilitate improved image reconstruction and further processing to provide improved diagnostic accuracy.

Certain examples provide an image processing apparatus including an artificial intelligence classifier. The classifier can detect, segment, and quantify pathology, for example. The classifier can be a discrete output of positive or negative for a finding, a segmentation, etc. For example, the classifier can instantiate machine learning and/or other artificial intelligence to generate a quantification from segmentation, such as a generated mask of a region of interest for disease D, in which the area of the region of interest is equal to X pixels or Y millimeters (mm), etc.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

Certain examples use neural networks and/or other machine learning to implement a new workflow for image and associated patient analysis including generating alerts based on radiological findings that may be generated and delivered at the point of care of a radiology exam. Certain examples use Artificial Intelligence (AI) algorithms to process one or more imaging exams (e.g., an image or set of images), and provide an alert based on the automated exam analysis. The alert(s) (e.g., including notification(s), recommendation(s), other action(s), etc.) may be intended for the technologist acquiring the exam, clinical team providers (e.g., nurse, doctor, etc.), radiologist, administration, operations, and/or even the patient. The alerts may be to indicate a specific or multiple quality control and/or radiological finding(s) or lack thereof in the exam image data, for example.

In certain examples, the AI algorithm can be (1) embedded within an imaging device, (2) running on a mobile device (e.g., a tablet, smart phone, laptop, other handheld or mobile computing device, etc.), and/or (3) running in a cloud (e.g., on premise or off premise) and delivers the alert via a web browser (e.g., which may appear on the radiology system, mobile device, computer, etc.). Such configurations can be vendor neutral and compatible with legacy imaging systems. For example, if the AI processor is running on a mobile device and/or in the "cloud", the configuration can receive the images (A) from the x-ray and/or other imaging system directly (e.g., set up as secondary push destination such as a Digital Imaging and Communications in Medicine (DICOM) node, etc.), (B) by tapping into a Picture Archiving and Communication System (PACS) destination for redundant image access, (C) by retrieving image data via a sniffer methodology (e.g., to pull a DICOM image off the system once it is generated), etc.

Certain examples provide apparatus, systems, methods, etc., to determine progression of a disease and/or other condition based on output of an algorithm instantiated using and/or driven by an artificial intelligence (AI) model, such as a deep learning network model, machine learning network model, etc. For example, a disease progression can be determined based on an output of an AI detection algorithm that includes three or more severity classes.

Certain examples provide apparatus, systems, and methods to determine progression of a disease and/or abnormality based on an AI detection algorithm, such as by comparing AI processing output(s) from a prior image acquisition with AI processing output(s) for a current image acquisition, to determine whether a severity class associated with the AI processing output is worsening or improving. Based on the severity class, an alert can be modified to indicate when an associated condition is worsening. For a meaningful change in severity class and alert status, at least three severity classes should exist as potential outputs of the AI detection algorithm, for example.

Thus, certain examples provide systems and methods to determine a progression of a disease, abnormality, condition, etc., based on an AI classification algorithm applied to a patient's image data. An example method includes determining a first classification result from an AI classification algorithm from the patient's prior image data; determining a second classification result from the AI classification algorithm from the patient's current image data; determining a change between the first classification result and the second classification result; and generating an alert for a caregiver based on the change if the change corresponds to worsening of the disease or abnormality or condition. The AI classification algorithm is trained at least three classes of severity associated with the disease, abnormality, condition, etc.

For example, a measure of severity (e.g., none, small, large, etc.) at a first time is compared to a measure of severity at a second time, and an evaluation of the difference in severity is used to trigger, when applicable, an alert. For example:

AI_Output_Severity_Time2 − AI_Output_Severity_Time1 = Small − Small = No Disease Progression = No Alert
AI_Output_Severity_Time2 − AI_Output_Severity_Time1 = Large − Small = Disease Improving = No Alert
AI_Output_Severity_Time2 − AI_Output_Severity_Time1 = Small − Large = Disease Worsening = Alert
AI_Output_Severity_Time2 − AI_Output_Severity_Time1 = None − Small = Disease Worsening = Alert As shown in the chart above, if the output severity remains small from time 1 to time 2, then the disease has not progressed, and no alert is to be generated. If the AI-generated severity was large and then becomes small, then the patient's progress against the disease is improving, so no alert is to be generated. However, if the AI-generated severity starts as small but becomes large, then the disease is worsening, and an alert is generated. Similarly, if the severity at a second time is small but the severity at a first time was none, then the disease is worsening, and an alert is generated.

For example, patients in a critical care setting frequently receive daily chest x-rays to monitor the progression or improvement of lung conditions such as plural effusion (fluid around the lung), consolidation (pneumonia), pneumothorax (lung collapse), etc. If a patient's condition worsens rapidly between subsequent chest x-rays, it is an indication to the medical team to conduct fast intervention, as the patient may be, or will soon be, in a critical condition. Interventions that may be conducted based on this interval change range from a medication change, to pulmonary aspiration or a thoracostomy (chest tube), for example. An artificial intelligence classifier can detect a presence or absence of disease, abnormality, etc., and be used to evaluate a progression of such disease, abnormality, etc. An alert can be generated and output at a point of care, on a device (e.g., an imaging device, an imaging workstation, etc.) to notify and/or otherwise provide instructions to a clinical care team, for example.

Rather than simply detect a current-state presence or absence of a disease, abnormality, condition, etc., a progression of that disease, abnormality, condition, etc., can be quantified, and an outcome can be projected. Thus, more accurate alerts can be generated, and false alarms, as well as false sense of security, can be avoided. For example, when a patient has had a persistent small pneumothorax for three days in a row, the clinical care team would continuously be alerted because the pneumothorax is present. However, the patient's condition has been stable. On day four, however, the small pneumothorax may become a large one, and a binary detection algorithm would simply continue to give the same alerts as the prior days—pneumothorax present—without alerting the team to the change and worsening problem, for example. Instead, certain examples provide technological improvements in artificial intelligence modeling, image data analysis, progression, and alerting to quantify a degree of change after presence of a disease, condition, abnormality, etc., has been detected. For example, a disease such as a pneumothorax can be quantified as a percentage of lung volume occupied by the pneumothorax. Thus, disease progression corresponds to a change in disease volume as a percentage of occupied lung volume, for example.

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, classified and further annotated for object localization, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

II. Description of Examples

Example Disease Analysis and Progression Systems

FIG. 1 illustrates an example condition comparator apparatus 100 including a plurality of input 110, 115, an artificial intelligence (AI) classifier 120, and an output comparator 130. Each input 110, 115 is provided to the AI classifier 120 (e.g., input 110 at time t0 and input 115 at time t1, etc.), which classifies image and/or other information in the respective input 110, 115 to identify a disease, abnormality, and/or other condition in the input 110, 115 and to generate a severity of the identified disease, abnormality, and/or other condition based on the input 110, 115. Using the example comparator apparatus 100, a condition can be identified and quantified in association with a severity and/or other state criterion, such as low/medium/high, none/small/large, none/small/medium/large, normal/abnormal/urgent, etc., at a plurality of times, and the plurality of time-based quantifications/classifications can be compared to determine a trend and trigger a next action, such as an alert, an order, an adjustment, etc.

Figure 2:
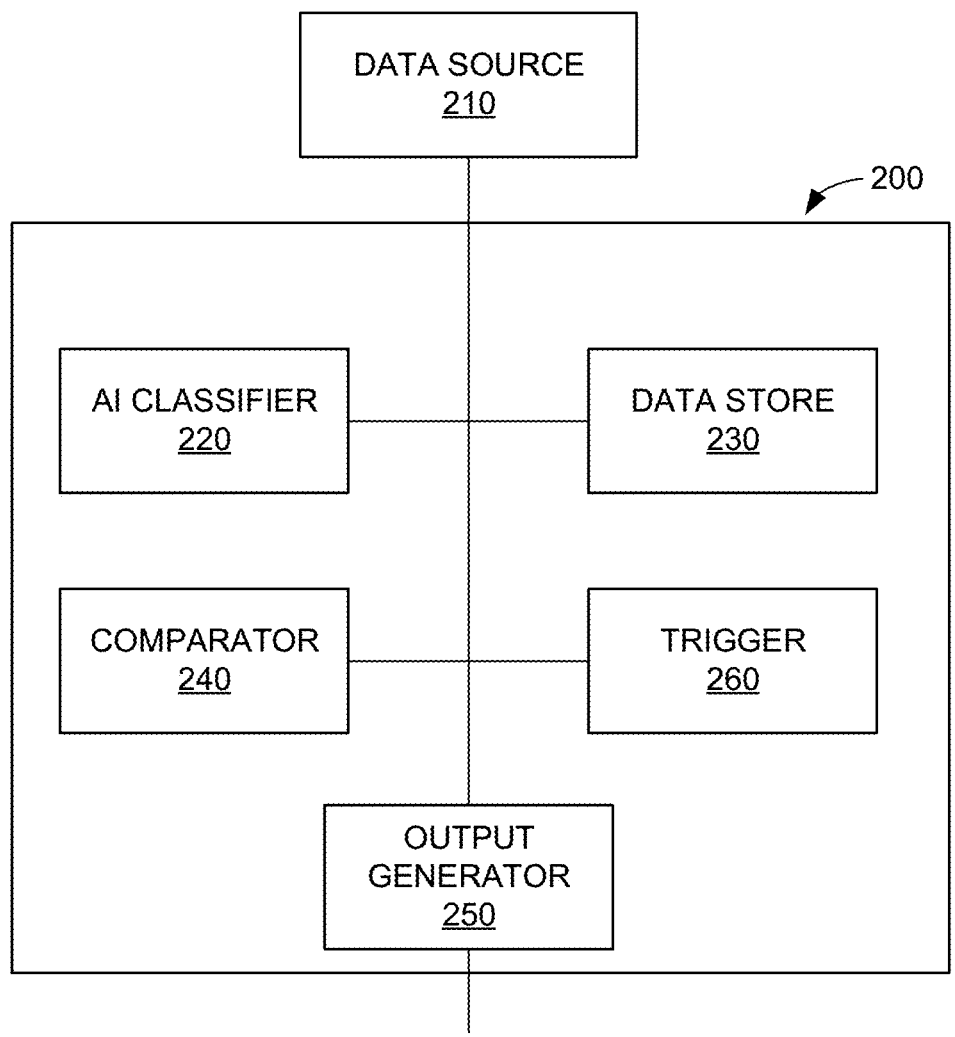
FIG. 2 illustrates an example clinical progression analysis apparatus.

FIG. 2 illustrates an example clinical progression analysis apparatus 200 that can be constructed based on the example condition comparator 100 of FIG. 1. The example apparatus 200 includes a data source 210, an artificial intelligence (AI) classifier 220, a data store 230, a comparator 240, an output generator 250, and a trigger 260. Input 110, 115 can be provided by the data source 210 (e.g., a storage device, an imaging device, etc., incorporated in and/or otherwise connected to the apparatus 200, etc.) to the AI classifier 220.

The example classifier 220 processes input over time to correlate input from the data source 210 with a severity and/or other classification. Thus, the AI classifier 220 processes input image data and/or other data to identify a disease, abnormality, and/or other condition in the input data and classify that disease/abnormality/condition according to one or more severity levels or states (e.g., low/medium/high, none/small/large, etc.) as specified by an equation, a threshold, and/or other criterion. For example, a pneumothorax has a severity state based on a percentage of lung volume occupied by the pneumothorax. Output of the AI classifier 220 can be stored in the data store 230, for example.

Over time, severity classifications made by the AI classifier 220 with respect to the same type of input 110, 115 from the data source 210 (e.g., lung MR images of the same patient taken at times t0 and t1, etc.) can be generated and stored in the data store 230. The classifications are provided to the comparator 240, which compares a classification at two or more different times (e.g., a first determined severity for a first set of image data from a first patient at time t0 compared to a second determined severity for a second set of image data from the first patient at time t1 and compared to a third determined severity for a third set of image data from the first patient at time t2, etc.) to determine a trend or progression in the disease, abnormality, and/or other condition associated with the classifications. For example, the size of a pneumothorax in a patient can be non-existent at time t0, small at time t1, and large at time t2, indicating a worsening progression of the pneumothorax condition.

The comparator 240 provides a result indicative of the trend/progression. The output generator 250 transforms that result into an output that can be displayed, stored, provided to another system for further processing such as an alert, an order, an adjustment in patient care, (e.g., a point of care alert system, an imaging/radiology workstation, a computer-aided diagnosis (CAD) processor, a scheduling system, a medical device, etc.), etc.

The trigger 260 coordinates actions among the data source 210, the AI classifier 220, the data store 230, the comparator 240, and the output generator 250. The trigger 260 can initiate input of data from the data source 210 to the classifier 220, comparison of results from the data store 230 by the comparator 240, output by the output generator 250. Thus, the trigger 260 serves as a coordinator among elements of the apparatus 200.

Example Learning Network Systems

Figure 3:
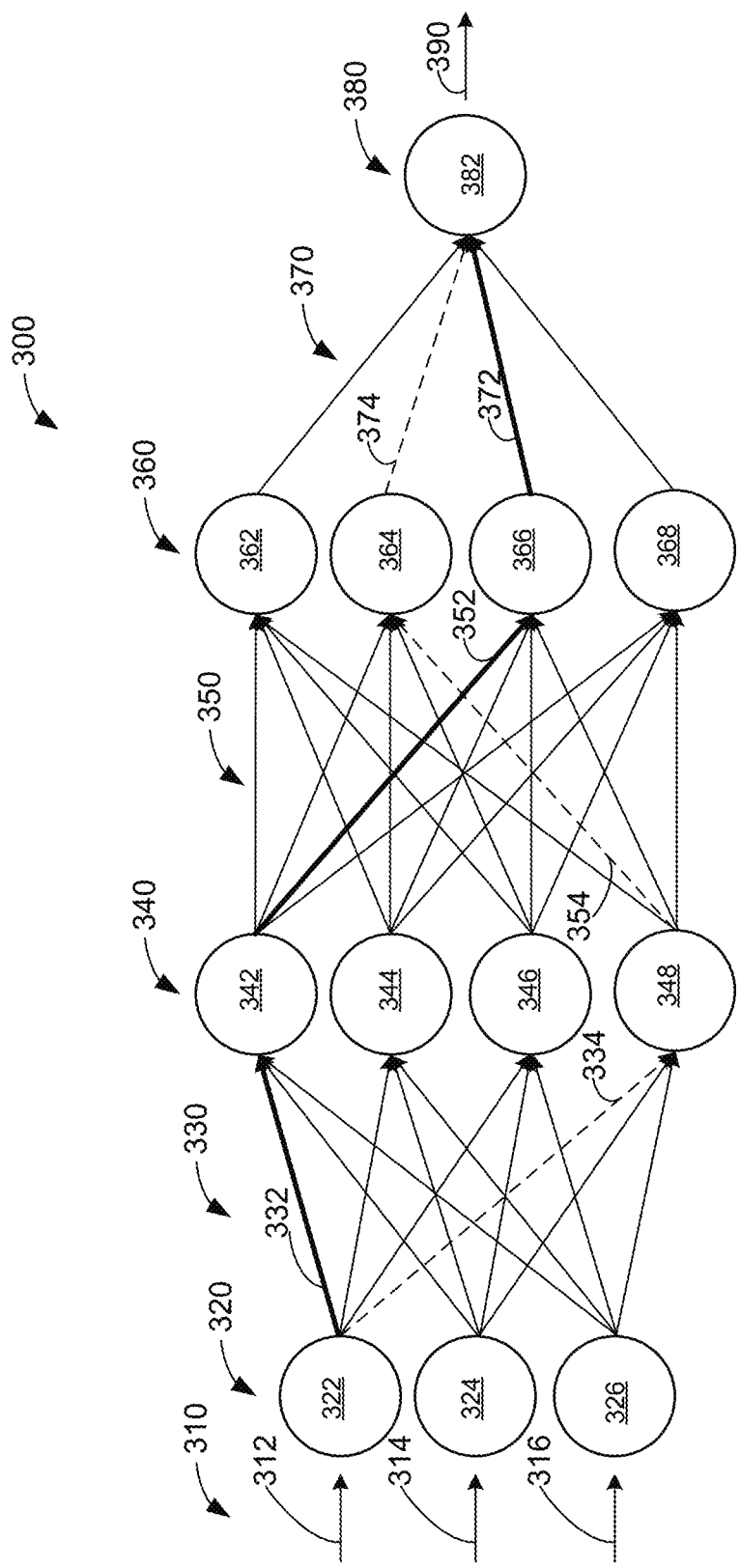
FIG. 3 is a representation of an example learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 and to an output 390.

The layer 320 is an input layer that, in the example of FIG. 3, includes a plurality of nodes 322, 324, 326. The layers 340 and 360 are hidden layers and include, the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370 certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Figure 4:
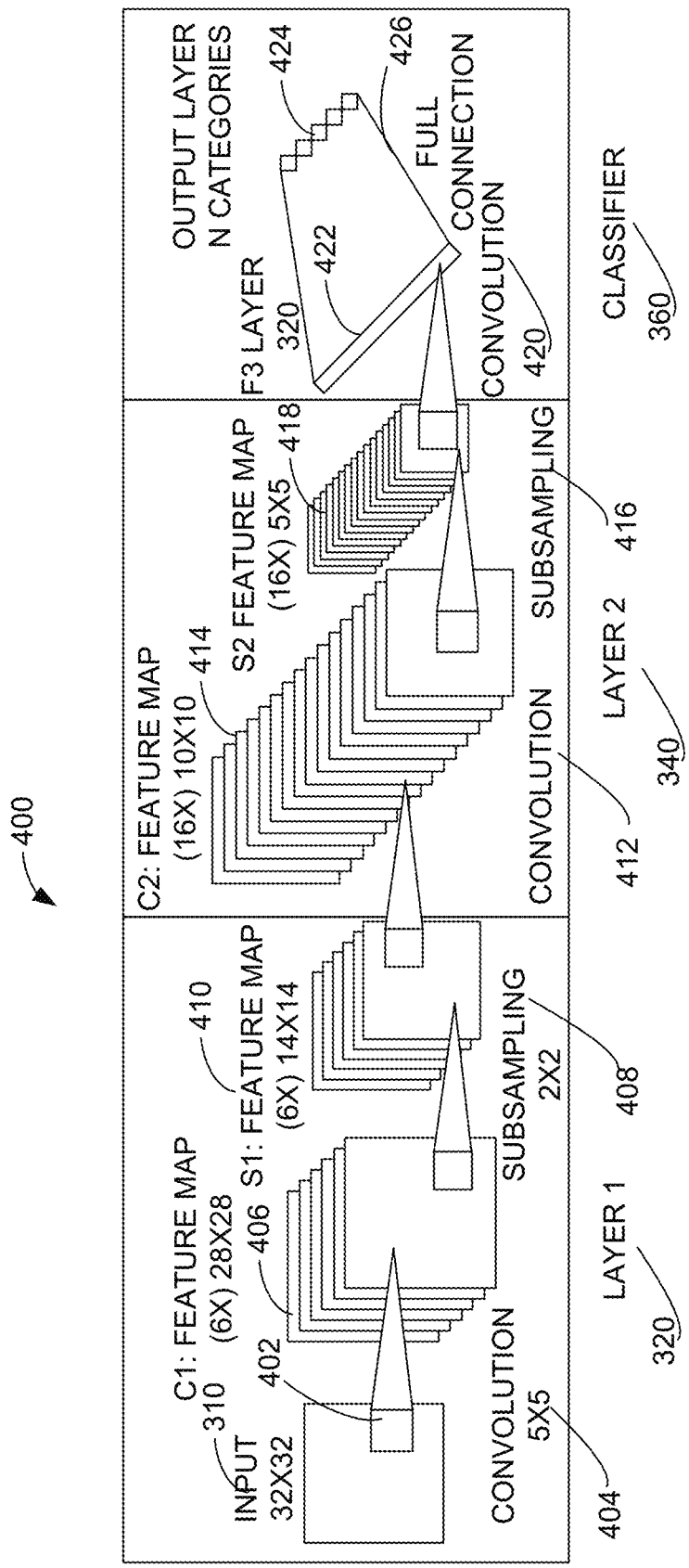
FIG. 4 illustrates a particular implementation of the example neural network as a convolutional neural network.

FIG. 4 illustrates a particular implementation of the example neural network 300 as a convolutional neural network 400. As shown in the example of FIG. 4, an input 310 is provided to the first layer 320 which processes and propagates the input 310 to the second layer 340. The input 310 is further processed in the second layer 340 and propagated to the third layer 360. The third layer 360 categorizes data to be provided to the output layer e80. More specifically, as shown in the example of FIG. 4, a convolution 404 (e.g., a 5×5 convolution, etc.) is applied to a portion or window (also referred to as a "receptive field") 402 of the input 310 (e.g., a 32×32 data input, etc.) in the first layer 320 to provide a feature map 406 (e.g., a (6×) 28×28 feature map, etc.). The convolution 404 maps the elements from the input 310 to the feature map 406. The first layer 320 also provides subsampling (e.g., 2×2 subsampling, etc.) to generate a reduced feature map 410 (e.g., a (6×) 14×14 feature map, etc.). The feature map 410 undergoes a convolution 412 and is propagated from the first layer 320 to the second layer 340, where the feature map 410 becomes an expanded feature map 414 (e.g., a (16×) 10×10 feature map, etc.). After subsampling 416 in the second layer 340, the feature map 414 becomes a reduced feature map 418 (e.g., a (16×) 4×5 feature map, etc.). The feature map 418 undergoes a convolution 420 and is propagated to the third layer 360, where the feature map 418 becomes a classification layer 422 forming an output layer of N categories 424 with connection 426 to the convoluted layer 422, for example.

Figure 5:
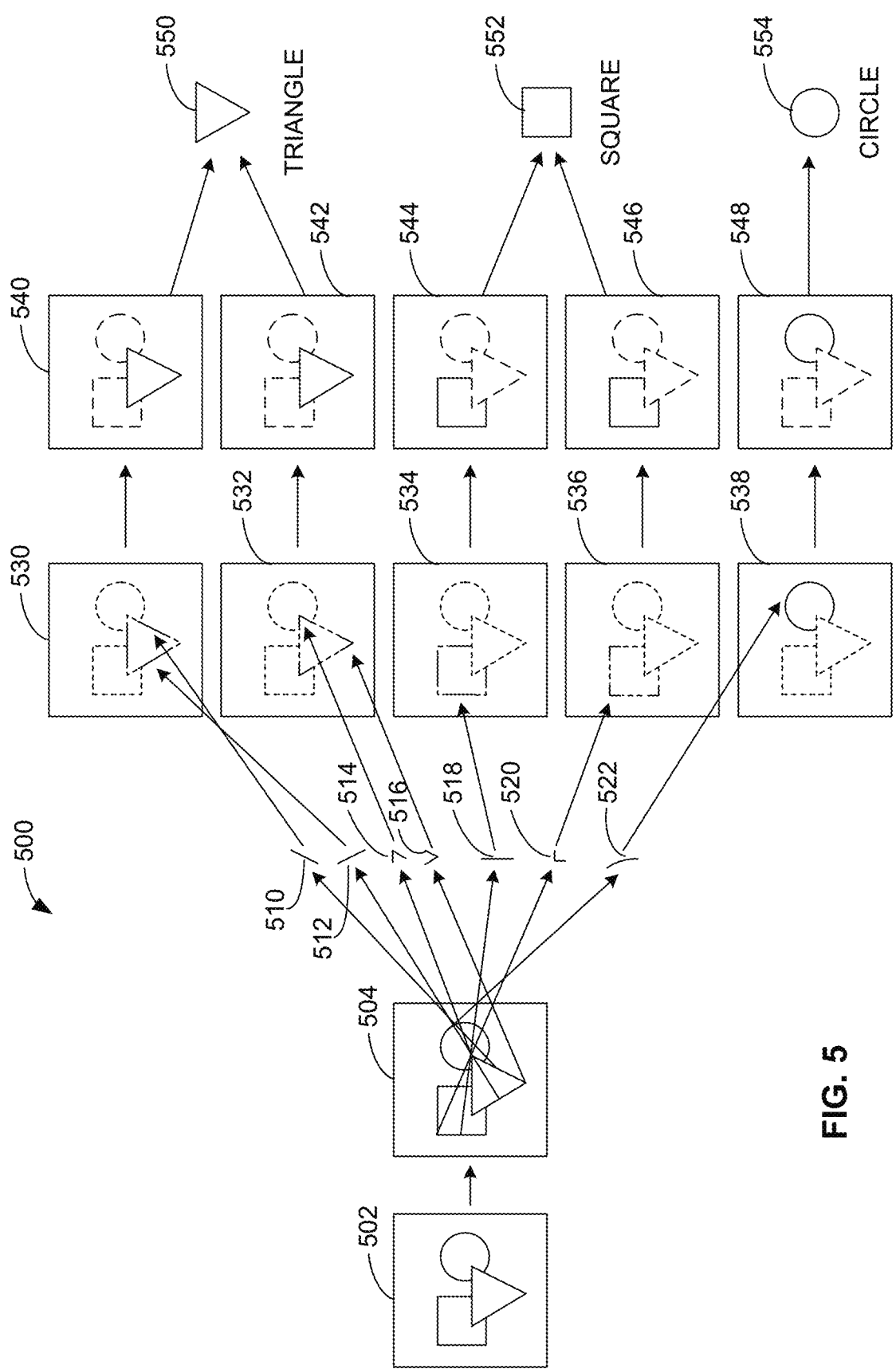
FIG. 5 is a representation of an example implementation of an image analysis convolutional neural network.

FIG. 5 is a representation of an example implementation of an image analysis convolutional neural network 500. The convolutional neural network 500 receives an input image 502 and abstracts the image in a convolution layer 504 to identify learned features 510-522. In a second convolution layer 530, the image is transformed into a plurality of images 530-538 in which the learned features 510-522 are each accentuated in a respective sub-image 530-538. The images 530-538 are further processed to focus on the features of interest 510-522 in images 540-548. The resulting images 540-548 are then processed through a pooling layer which reduces the size of the images 540-548 to isolate portions 550-554 of the images 540-548 including the features of interest 510-522. Outputs 550-554 of the convolutional neural network 500 receive values from the last non-output layer and classify the image based on the data received from the last non-output layer. In certain examples, the convolutional neural network 500 may contain many different variations of convolution layers, pooling layers, learned features, and outputs, etc.

Figure 6A:
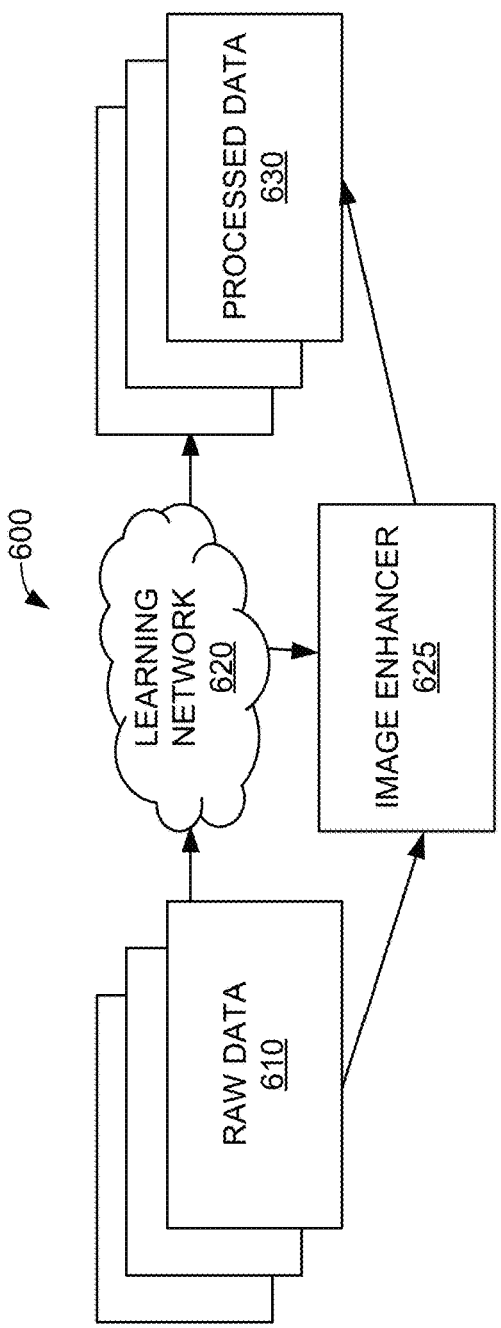
FIG. 6A illustrates an example configuration to apply a learning network to process and/or otherwise evaluate an image.

FIG. 6A illustrates an example configuration 600 to apply a learning (e.g., machine learning, deep learning, etc.) network to process and/or otherwise evaluate an image. Machine learning can be applied to a variety of processes including image acquisition, image reconstruction, image analysis/diagnosis, etc. As shown in the example configuration 600 of FIG. 6A, raw data 610 (e.g., raw data 610 such as sonogram raw data, etc., obtained from an imaging scanner such as an x-ray, computed tomography, ultrasound, magnetic resonance, etc., scanner) is fed into a learning network 620. The learning network 620 processes the data 610 to correlate and/or otherwise combine the raw data 620 into processed data 630 (e.g., a resulting image, etc.) (e.g., a "good quality" image and/or other image providing sufficient quality for diagnosis, etc.). The learning network 620 includes nodes and connections (e.g., pathways) to associate raw data 610 with the processed data 630. The learning network 620 can be a training network that learns the connections and processes feedback to establish connections and identify patterns, for example. The learning network 620 can be a deployed network that is generated from a training network and leverages the connections and patterns established in the training network to take the input raw data 610 and generate the resulting image 630, for example.

Once the learning 620 is trained and produces good images 630 from the raw image data 610, the network 620 can continue the "self-learning" process and refine its performance as it operates. For example, there is "redundancy" in the input data (raw data) 610 and redundancy in the network 620, and the redundancy can be exploited.

If weights assigned to nodes in the learning network 620 are examined, there are likely many connections and nodes with very low weights. The low weights indicate that these connections and nodes contribute little to the overall performance of the learning network 620. Thus, these connections and nodes are redundant. Such redundancy can be evaluated to reduce redundancy in the inputs (raw data) 610. Reducing input 610 redundancy can result in savings in scanner hardware, reduced demands on components, and also reduced exposure dose to the patient, for example.

In deployment, the configuration 600 forms a package 600 including an input definition 610, a trained network 620, and an output definition 630. The package 600 can be deployed and installed with respect to another system, such as an imaging system, analysis engine, etc. An image enhancer 625 can leverage and/or otherwise work with the learning network 620 to process the raw data 610 and provide a result (e.g., processed image data and/or other processed data 630, etc.). The pathways and connections between nodes of the trained learning network 620 enable the image enhancer 625 to process the raw data 610 to form the image and/or other processed data result 630, for example.

Figure 6B:
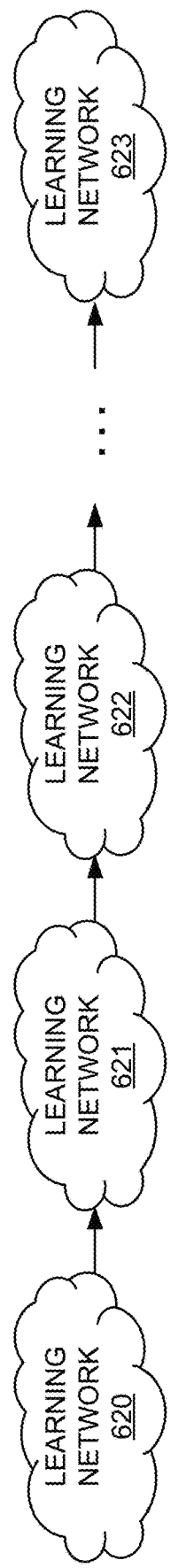
FIG. 6B illustrates a combination of a plurality of learning networks.

As shown in the example of FIG. 6B, the learning network 620 can be chained and/or otherwise combined with a plurality of learning networks 621-623 to form a larger learning network. The combination of networks 620-623 can be used to further refine responses to inputs and/or allocate networks 620-623 to various aspects of a system, for example.

In some examples, in operation, "weak" connections and nodes can initially be set to zero. The learning network 620 then processes its nodes in a retaining process. In certain examples, the nodes and connections that were set to zero are not allowed to change during the retraining. Given the redundancy present in the network 620, it is highly likely that equally good images will be generated. As illustrated in FIG. 6B, after retraining, the learning network 620 becomes DLN 621. The learning network 621 is also examined to identify weak connections and nodes and set them to zero. This further retrained network is learning network 622. The example learning network 622 includes the "zeros" in learning network 621 and the new set of nodes and connections. The learning network 622 continues to repeat the processing until a good image quality is reached at a learning network 623, which is referred to as a "minimum viable net (MVN)". The learning network 623 is a MVN because if additional connections or nodes are attempted to be set to zero in learning network 623, image quality can suffer.

Once the MVN has been obtained with the learning network 623, "zero" regions (e.g., dark irregular regions in a graph) are mapped to the input 610. Each dark zone is likely to map to one or a set of parameters in the input space. For example, one of the zero regions may be linked to the number of views and number of channels in the raw data. Since redundancy in the network 623 corresponding to these parameters can be reduced, there is a highly likelihood that the input data can be reduced and generate equally good output. To reduce input data, new sets of raw data that correspond to the reduced parameters are obtained and run through the learning network 621. The network 620-623 may or may not be simplified, but one or more of the learning networks 620-623 is processed until a "minimum viable input (MVI)" of raw data input 610 is reached. At the MVI, a further reduction in the input raw data 610 may result in reduced image 630 quality. The MVI can result in reduced complexity in data acquisition, less demand on system components, reduced stress on patients (e.g., less breath-hold or contrast), and/or reduced dose to patients, for example.

By forcing some of the connections and nodes in the learning networks 620-623 to zero, the network 620-623 to build "collaterals" to compensate. In the process, insight into the topology of the learning network 620-623 is obtained. Note that network 621 and network 622, for example, have different topology since some nodes and/or connections have been forced to zero. This process of effectively removing connections and nodes from the network extends beyond "deep learning" and can be referred to as "deep-deep learning", for example.

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 7:
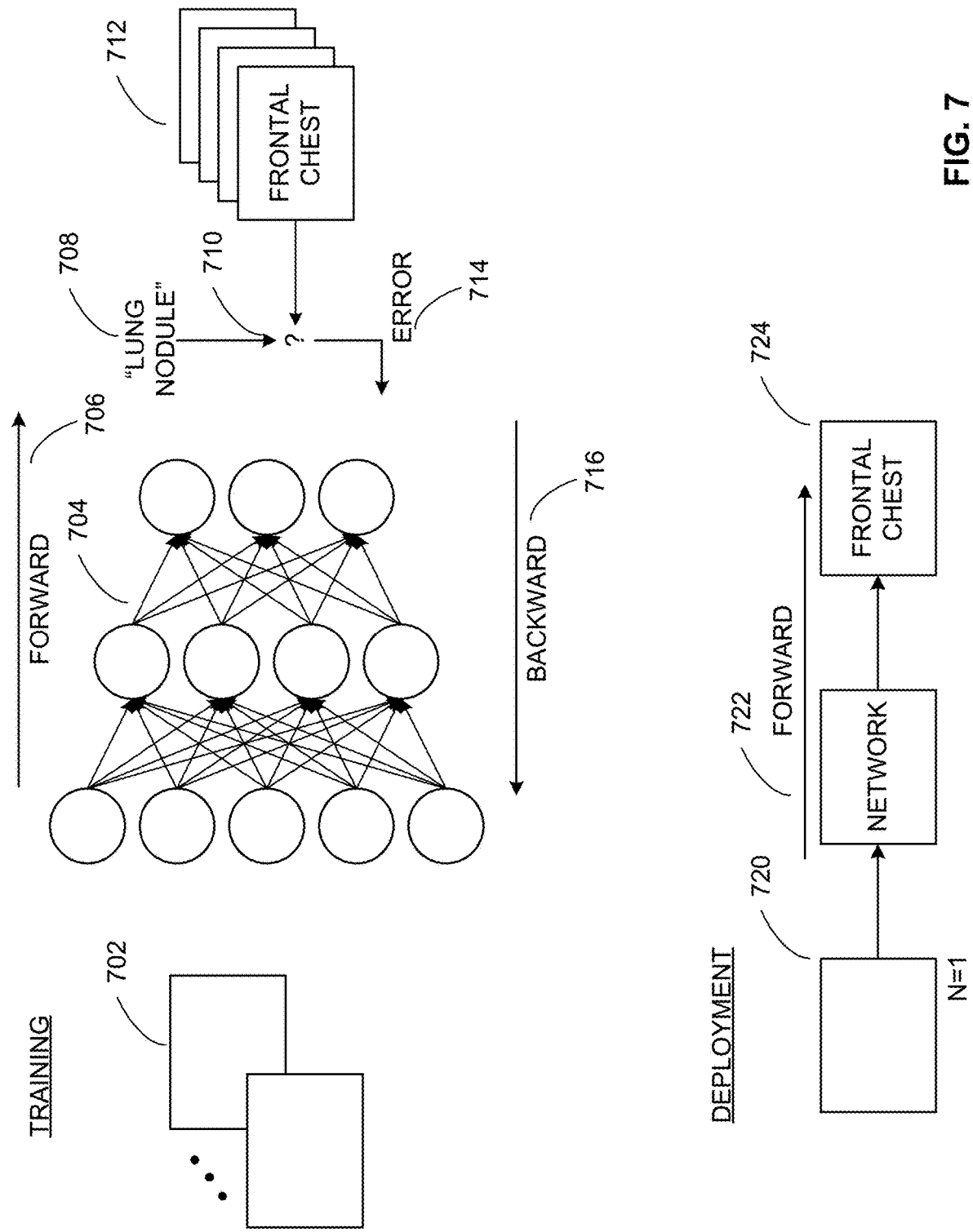
FIG. 7 illustrates example training and deployment phases of a learning network.

FIG. 7 illustrates example training and deployment phases of a learning network, such as a deep learning or other machine learning network. As shown in the example of FIG. 7, in the training phase, a set of inputs 702 is provided to a network 704 for processing. In this example, the set of inputs 702 can include facial features of an image to be identified. The network 704 processes the input 702 in a forward direction 706 to associate data elements and identify patterns. The network 704 determines that the input 702 represents a lung nodule 708. In training, the network result 708 is compared 710 to a known outcome 712. In this example, the known outcome 712 is a frontal chest (e.g., the input data set 702 represents a frontal chest identification, not a lung nodule). Since the determination 708 of the network 704 does not match 710 the known outcome 712, an error 714 is generated. The error 714 triggers an analysis of the known outcome 712 and associated data 702 in reverse along a backward pass 716 through the network 704. Thus, the training network 704 learns from forward 706 and backward 716 passes with data 702, 712 through the network 704.

Once the comparison of network output 708 to known output 712 matches 710 according to a certain criterion or threshold (e.g., matches n times, matches greater than x percent, etc.), the training network 704 can be used to generate a network for deployment with an external system. Once deployed, a single input 720 is provided to a deployed learning network 722 to generate an output 724. In this case, based on the training network 704, the deployed network 722 determines that the input 720 is an image of a frontal chest 724.

Figure 8:
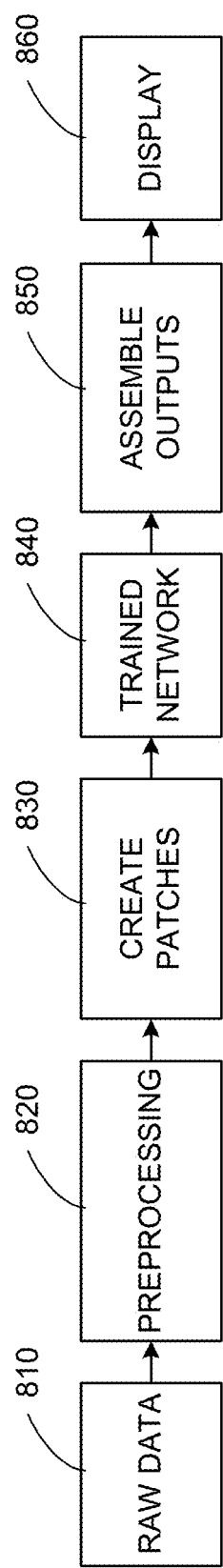
FIG. 8 illustrates an example product leveraging a trained network package to provide a deep learning product offering.

FIG. 8 illustrates an example product leveraging a trained network package to provide a deep and/or other machine learning product offering. As shown in the example of FIG. 8, an input 810 (e.g., raw data) is provided for preprocessing 820. For example, the raw input data 810 is preprocessed 820 to check format, completeness, etc. Once the data 810 has been preprocessed 820, patches are created 830 of the data. For example, patches or portions or "chunks" of data are created 830 with a certain size and format for processing. The patches are then fed into a trained network 840 for processing. Based on learned patterns, nodes, and connections, the trained network 840 determines outputs based on the input patches. The outputs are assembled 850 (e.g., combined and/or otherwise grouped together to generate a usable output, etc.). The output is then displayed 860 and/or otherwise output to a user (e.g., a human user, a clinical system, an imaging modality, a data storage (e.g., cloud storage, local storage, edge device, etc.), etc.).

Figure 9A:
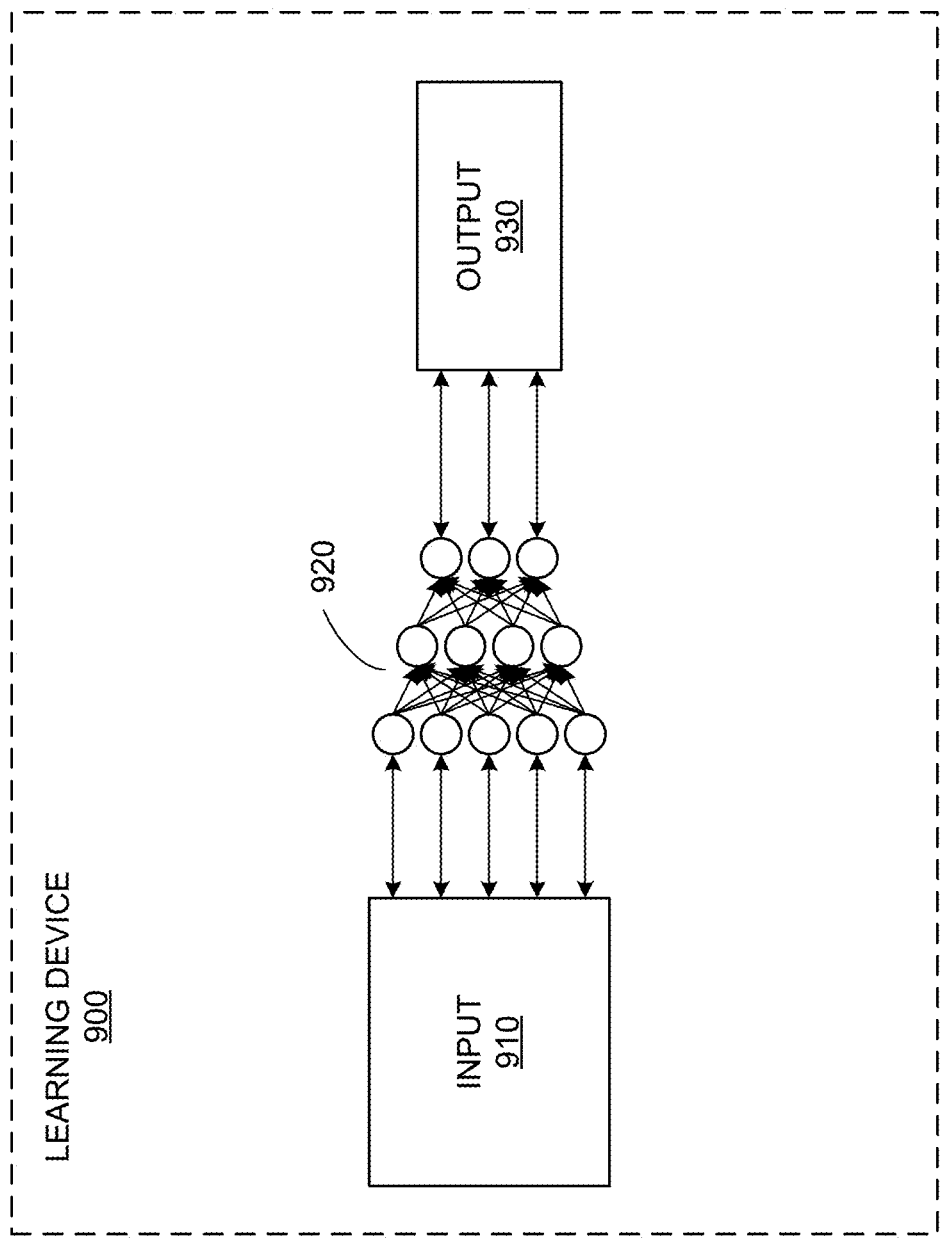
FIGS. 9A-9C illustrate various deep learning device configurations.
Figure 9B:
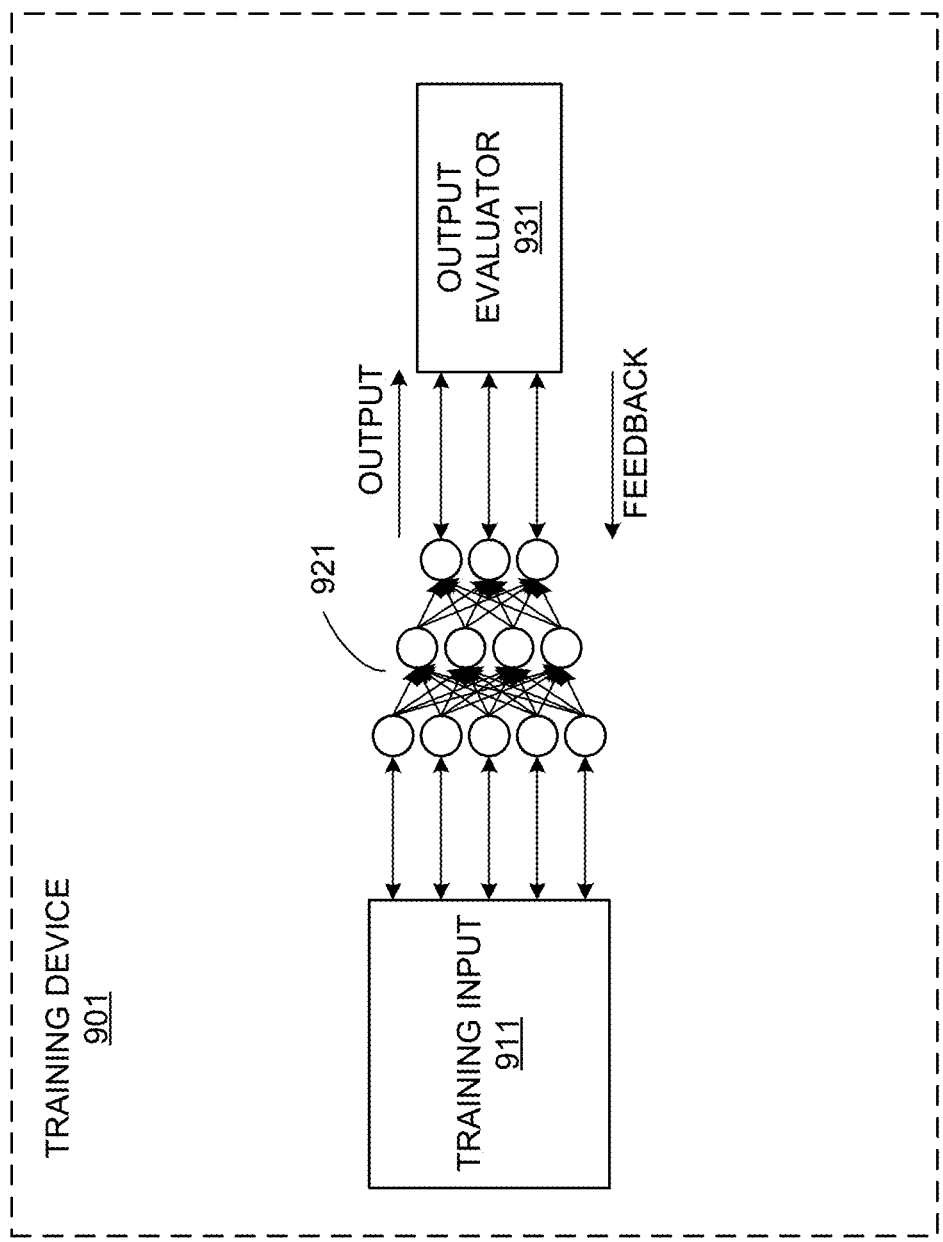
Figure 9C:
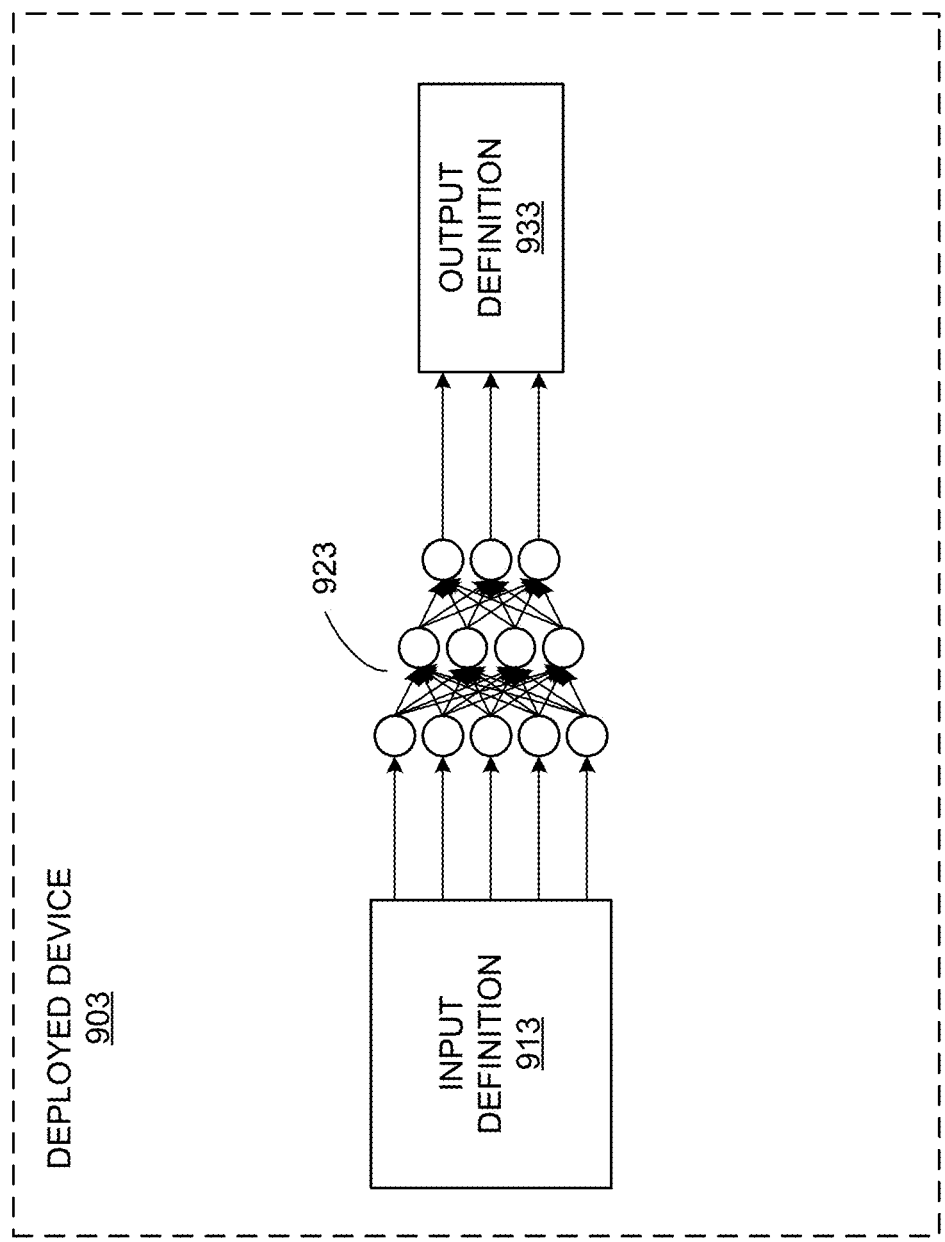

As discussed above, learning networks can be packaged as devices for training, deployment, and application to a variety of systems. FIGS. 9A-9C illustrate various learning device configurations. For example, FIG. 9A shows a general learning device 900. The example device 900 includes an input definition 910, a learning network model 920, and an output definition 930. The input definition 910 can include one or more inputs translating into one or more outputs 930 via the network 920.

FIG. 9B shows an example training device 901. That is, the training device 901 is an example of the device 900 configured as a training learning network device. In the example of FIG. 9B, a plurality of training inputs 911 are provided to a network 921 to develop connections in the network 921 and provide an output to be evaluated by an output evaluator 931. Feedback is then provided by the output evaluator 931 into the network 921 to further develop (e.g., train) the network 921. Additional input 911 can be provided to the network 921 until the output evaluator 931 determines that the network 921 is trained (e.g., the output has satisfied a known correlation of input to output according to a certain threshold, margin of error, etc.).

FIG. 9C depicts an example deployed device 903. Once the training device 901 has learned to a requisite level, the training device 901 can be deployed for use. While the training device 901 processes multiple inputs to learn, the deployed device 903 processes a single input to determine an output, for example. As shown in the example of FIG. 9C, the deployed device 903 includes an input definition 913, a trained network 923, and an output definition 933. The trained network 923 can be generated from the network 921 once the network 921 has been sufficiently trained, for example. The deployed device 903 receives a system input 913 and processes the input 913 via the network 923 to generate an output 933, which can then be used by a system with which the deployed device 903 has been associated, for example.

Example Image Processing and Classification Systems and Methods

In certain examples, disease, abnormality, and/or other condition identification and progression can be determined through AI-driven analysis of associated image data for a patient.

Figure 10:
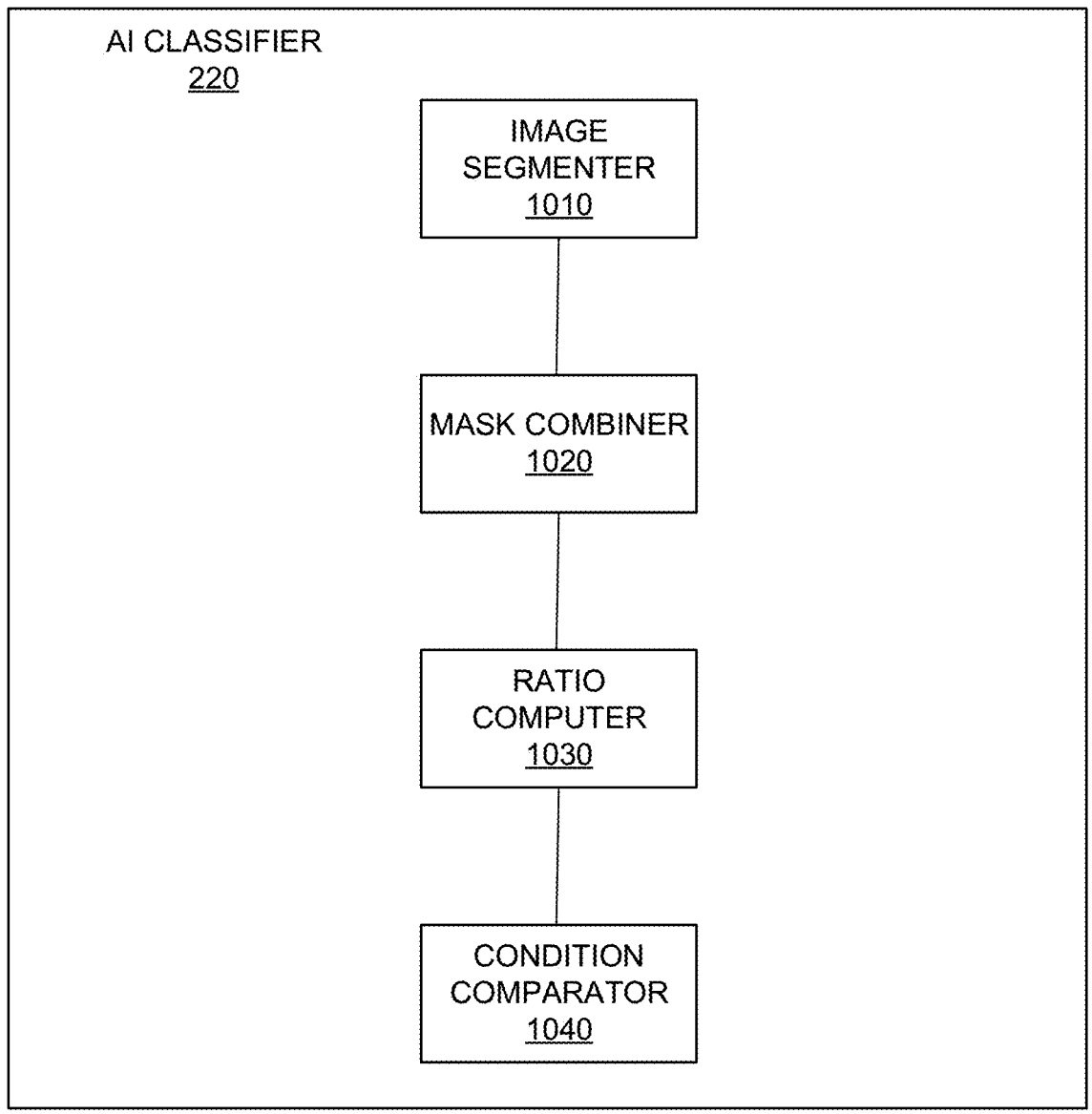
FIG. 10 illustrates an example implementation of the artificial intelligence classifier of FIG. 2 to process image data to be used by an artificial intelligence model to quantify a disease, abnormality, and/or other condition.

FIG. 10 illustrates an example implementation of the AI classifier 220 to process image data to be used by an AI model to quantify a disease, abnormality, and/or other condition. The example implementation of the classifier 220 enables annotation of one or more images including an organ region and a region of interest within the organ region. The example classifier 220 of FIG. 10 includes an image segmenter 1010, a mask combiner 1020, a ratio computer 1030, and a condition comparator 1040.

The example image segmenter 1010 is to identify a first mask and a second mask in an input image. For example, the image segmenter 1010 processes the image to segment a region of interest within an organ region identified in the image to obtain a first mask. The first mask is a segmentation mask is a filter that includes the region of interest in the image and excludes the remainder of the image. The mask can be applied to image data to exclude all but the region of interest, for example. The mask can be obtained using a convolutional neural network model, for example, such as the network 400, 500 shown in FIGS. 4-5, a generative adversarial network, etc. The image segmenter 1010 further processes the image to segment the organ region according to one or more criterion to obtain a second mask. For example, the second mask can represent the organ region, an area of the organ region outside the region of interest, etc.

For example, if the organ region is a lung, and the region of interest is a pneumothorax identified in the lung (e.g., by a contour of the lung and a contour of the collapsed area of the lung representing the pneumothorax, etc.), the first mask is generated to identify the pneumothorax, and the second mask is generated to identify the entire organ region.

The example combiner 1020 combines the first mask and the second mask and associated areas with annotation terms in the image. Annotations can be relative qualification terms to produce quantification, for example. For example, mask areas can be combined with descriptive terms such as foggy, patchy, dense, etc., to compute relative density values for the region of interest and organ region in the image. Image areas (e.g., areas of frontal and lateral images, etc.) can be combined to produce a volume metric, for example.

The example ratio computer 1030 computes a ratio based on the first mask and the second mask to quantify a region of interest in the image. For example, the ratio computer 1030 can compare an area of the region of interest (ROI) represented by the first mask to an area of the entire organ region represented by the second mask to determine a ratio of the ROI (e.g., the area of an identified pneumothorax, etc.) to the entire organ entire (e.g., the total lung volume, etc.). In another example, the ratio computer 1030 compares an area of the ROI represented by the first mask to a remainder of the organ region outside the ROI that is represented by the second mask to determine a ratio of the ROI (e.g., the area of an identified pneumothorax, etc.) to an area of the organ region outside the ROI (e.g., lung volume outside the pneumothorax, etc.).

The example condition comparator 1040 compares the ratio generated by the ratio computer 1030 to a standard, normal value, expected value, threshold, and/or other criterion to determine a severity of the disease/abnormality/condition. For example, the comparator 1040 compares a ratio of ½ for area of pneumothorax versus total lung area to a set of ratios defining a severity level/state of pneumothorax (e.g., none, small, large, etc.). A severity output of the condition comparator 1040 can be provided to the comparator 240 to determine a trend or progress of the associated disease, abnormality, and/or other condition, for example.

Thus, the AI classifier 220 can be configured to annotate a medical image or set of related medical image(s) for AI/machine learning/deep learning/CAD algorithm training, to quantify diseases, abnormalities, other conditions, etc. Such methods are consistent, repeatable methodologies which could replace common subjective methods of today, enabling automatic, accurate detection of a disease, and quantifying its severity and/or progression.

Certain examples evaluate a region of interest in an organ or other object on a relative basis. For example, a single time point quantification of a disease, abnormality, and/or other condition can be determined to classify severity of the disease, abnormality, or condition as well as track a progression of the disease, abnormality, or condition over various time points.

For example, the segmenter 1010 of the classifier 220 can segment an abnormal lung region and compute a corresponding area divided by an area segmentation of the affected lung's aerated area to produce a ratio percentage of the size of the abnormality with respect to the viable surrounding lung tissue. The ratio computer 1030 can generate the ratio percentage according to:

$$\text{Segmented Abnormality Area/Aerated Lung Segmented Area} = \% \text{ of Lung Area affected by Lung Disease/Abnormality.}$$

In another example, the segmenter 1010 can segment an abnormal lung region, which the ratio computer 130 divides by an area segmentation of the affected lung area to produce a ratio percentage of the size of the abnormality with respect to the total lung tissue such as:

$$\text{Segmented Abnormality Area/Total Lung Segmented Area} = \% \text{ of Lung Area affected by Lung Disease/Abnormality.}$$

In another example, the segmenter 1010 can segment an abnormal lung region, which the ratio computer 130 divides by an area segmentation of a fraction of the chest cavity area to produce a ratio percentage of the size of the abnormality with respect to the fraction of chest cavity such as:

$$\text{Segmented Abnormality Area/The fraction of chest cavity Area} = \% \text{ of Lung Area affected by Lung Disease/Abnormality.}$$

In another example, a segmented area metric of a pleural effusion can be combined by the mask combine 1020 with qualitative terms such as foggy, patchy, severe consolidation, etc., to produce a relative quantification of a density of the fluid.

In certain examples, an area of an abnormality alone (e.g., in pixels squared, millimeters squared, etc.) can be processed and subject to magnification correction using a marker and/or other reference object. However, such abnormality analysis does not qualify that an abnormality within a normal aerated lung is less of a concern than an abnormality within a lung that is only 50% aerated (e.g., indicating a compromised respiratory system), for example.

While example implementations are illustrated in conjunction with FIGS. 1-10, elements, processes and/or devices illustrated in conjunction with FIGS. 1-10 can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 11:
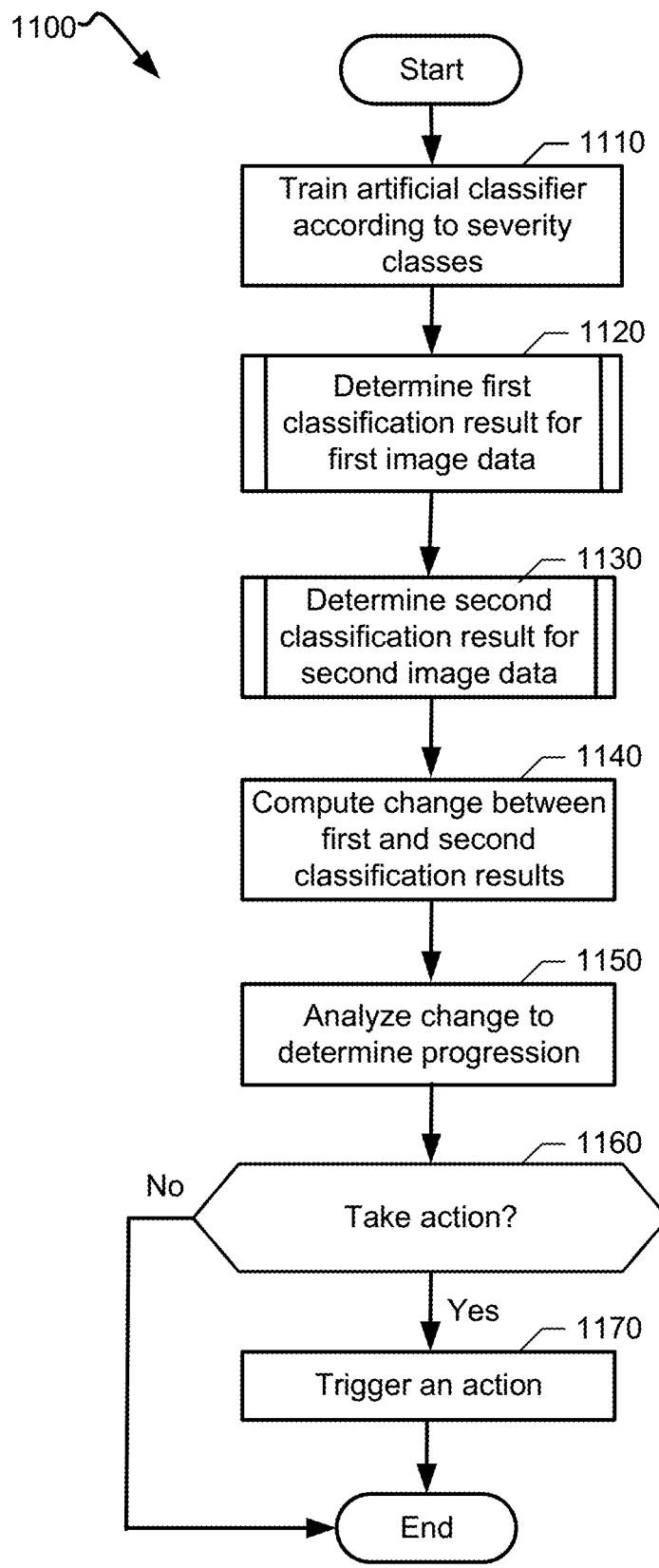
FIGS. 11-12 illustrate flow diagrams for example methods of automated processing and image analysis in accordance with the systems and/or apparatus of FIGS. 1-10.
Figure 12:
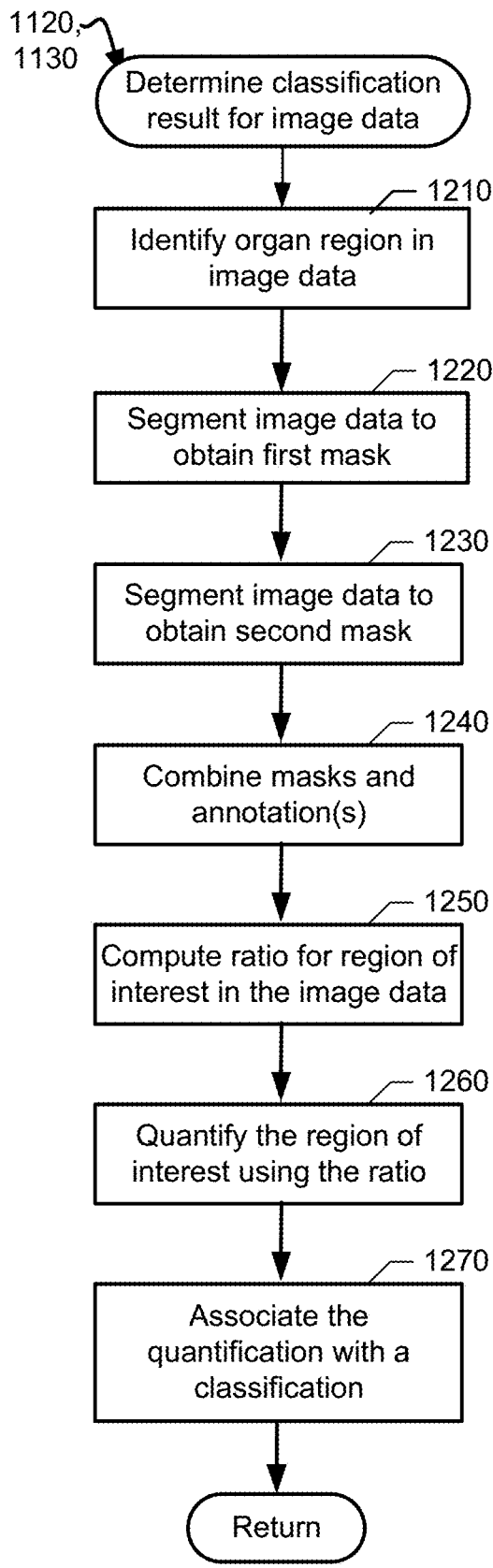

Flowcharts representative of example machine readable instructions for implementing components disclosed and described herein are shown in conjunction with at least FIGS. 11-12. In the examples, the machine readable instructions include a program for execution by a processor such as the processor 1312 shown in the example processor platform 1300 discussed below in connection with FIG. 13. The program may be embodied in machine readable instructions stored on a tangible computer readable storage medium such as a CD-ROM, a floppy disk, a hard drive, a digital versatile disk (DVD), a Blu-ray disk, or a memory associated with the processor 1312, but the entire program and/or parts thereof could alternatively be executed by a device other than the processor 1312 and/or embodied in firmware or dedicated hardware. Further, although the example program is described with reference to the flowcharts illustrated in conjunction with at least FIGS. 11-12, many other methods of implementing the components disclosed and described herein may alternatively be used. For example, the order of execution of the blocks may be changed, and/or some of the blocks described may be changed, eliminated, or combined. Although the flowcharts of at least FIGS. 11-12 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIGS. 11-12 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIGS. 11-12 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

As shown in the example method 1100 depicted in FIG. 11, condition severity and associated progression for a patient can be determined. At block 1110, an artificial intelligence classifier is trained according to a severity classification and/or other classification for a disease, abnormality, or condition. For example, the classifier 220 is trained to identify a pneumothorax in a lung image and to classify the pneumothorax as none, small, or large, based on a ratio of an area of the pneumothorax to total lung area (or to affected lung area), etc. Thus, as described above, the classifier 220 learns how to identify an organ region, region of interest within the organ region, and a severity classification through training and testing with "truthed" or verified image data such as image data that has been analyzed and annotated with location information, size, relationship, etc.

At block 1120, a first classification result is determined by applying an artificial intelligence classifier to first image data. At block 1130, a second classification result is determined by applying the artificial intelligence classifier to second image data. Thus, a trained and deployed deep learning network model and/or other artificial intelligence construct can process input image data with respect to one or more criterion (e.g., anatomy type, region, etc.) to generate a severity indicator and/or other classification (e.g., low/medium/high, none/small/large, small/medium/large, none/minor/major, etc.). Thus, by providing image data to a deep learning network model and/or other AI construct of the AI classifier 220, image data can be processed to generate classification result(s).

At block 1140, a change or difference between the first classification result and the second classification result is computed. For example, the comparator 240 compares the classification values for the first classification result and the second classification result to identify a change, delta, difference, etc., between the results (e.g., results obtained between two image data sets, at two different times, etc.). For example, the comparator 240 can compute a change from no pneumothorax to small pneumothorax, from minor tumor to major tumor, from large lesion to small lesion, etc., based on the set of two or more classification results.

At block 1150, the change in classification result is analyzed with respect to a defined progression of the disease, abnormality, or condition to determine a progression of this patient's disease, abnormality, or condition. The determined progression can correspond to a state such as no progression, improving, worsening, etc. For example, if the change is from none to small or large, then the progression is worsening. If the change is from large to small, the progression is improving, for example. If there is no change (e.g., an identified mass remains medium, etc.), then there is no progression, for example.

At block 1160, the determined progression is reviewed to determine whether an action is to be triggered. For example, the state of the determined progression is evaluated to determine whether an alert or other action is warranted. For example, an improved progression or no progression may not warrant any alert or other action (e.g., also referred to as a corrective action, etc.). However, a worsening progression may indicate that intervention is warranted.

When an action and/or other intervention is to be triggered, at block 1170, an action is triggered. For example, an alert can be generated (e.g., a log file alert, a clinical dashboard alert, an audible and/or visual alert to a healthcare practitioner, other notification, etc.) to notify a user, system, etc., of the determined progression (e.g., a worsening condition, etc.). For example, a nurse can be notified of a worsening pneumothorax, a test can be ordered for an enlarged lesion, an exam can be scheduled with a scheduling system for appearance of a mass where there was none before, etc.

FIG. 12 illustrates a flow diagram for example implementation of determining a first classification result (block 1120) and/or determining a second classification results (block 1130). At block 1210, an organ region is identified in image data. For example, image data can be processed by a convolutional neural network, other deep learning network model, and/or other artificial intelligence construct to identify a target organ region in one or more images included in the image data.

At block 1220, a region of interest within the organ region is segmented in the image data to obtain a first mask. For example, a pneumothorax identified in a lung or a portion of a lung can be masked in an image to isolate an area including the pneumothorax. At block 1230, the organ region is segmented according to one or more predetermined criterion to obtain a second mask. For example, the lung can be masked to exclude portions of the image outside the lung. Alternatively or in addition, a portion of the lung including the pneumothorax but less than the entire lung can be masked to isolate analysis on a portion of the lung whose function is impacted by the detected condition (e.g., the collapsed lung from pneumothorax), etc.

At block 1240, areas of the first and second segmented masks are combined along with relative qualification annotation terms to produce further quantification. For example, combining area of mask with descriptive terms such as foggy, patchy, dense, etc., to compute relative density values; combining areas of frontal and lateral images to produce volume metric etc. Thus, the combined masks can provide a model of a lung region affected by a pneumothorax as well as descriptors for density in that area of the image, etc.

At block 1250, a ratio metric is computed based on the first mask and the second mask. For example, a density of lung tissue in an area of pneumothorax can be compared to a density of normal lung tissue to determine a ratio. An area occupied by the pneumothorax can be compared to a remaining lung area/sub-area to compute a ratio, for example.

At block 1260, a region of interest in the image data is quantified using the ratio metric. For example, a pneumothorax can be quantified as 25% of lung area, 50% of lung area, 80% of lung area, etc. In another example, a size of a lesion relative to the surrounding organ can be quantified, etc.

At block 1270, the quantification of the region of interest is associated with a severity indicator and/or other classification. For example, a pneumothorax that occupies 20% of lung area can be classified as small. A pneumothorax that occupies 70% of lung area can be classified as large, for example. A severity classifier can be provided to the comparator 240 for analysis, for example.

Thus, certain examples provide an automated, deep/machine-learning driven processing of image data to determine severity and progression of a disease, abnormality, and/or other condition in a patient and/or patient population. With pneumothorax, for example, a collapse of the lung is difficult to detect and measure because severity of a 3D issue is difficult to evaluate from looking at a 2D image.

In an effort to overcome the limitations of subjective methods, measurement methods have been developed and proposed, such as the Rhea method, which determines the size of pneumothorax in the upright patients via an equation that considers various interpleural distances. The Rhea algorithm uses upright 2D images to build a CT regression, but patient position matters, and, while the Rhea algorithm is built around the assumption of an upright patient, most patients are instead laying in bed, rendering the approach ineffective. The Collins method provides quantification of pneumothorax size on chest radiographs (e.g., with patient lying down) using interpleural distances from a regression analysis based on volume measurements from a helical CT scan. The light method provides guidelines on the management of spontaneous pneumothorax, for example. All of these methods are insufficient for reliable, reproducible detection of a pneumothorax, for example.

With a pneumothorax, for example, air is present in the pleural space and indicates thoracic disease in the patient. Chest x-ray images can be used to identify the potential pneumothorax near a rib boundary based on texture, contour, pixel values, etc. An AI model in the classifier can assign a confidence score to that identification or inference based on the strength of available information indicating the presence of the pneumothorax, for example. Feedback can be provided from users to improve the AI pneumothorax detection model, for example. The AI model can be trained based on a variety of parameters/criterion such as size, severity, linear measurement (e.g., from wall of chest to plural line edge of collapsed lung), estimated percentage of lung volume (e.g., looks like a 10% collapse, 30% collapse, etc.), etc., which can vary depending on the patient's position for imaging and/or other measurement.

Using the AI classifier 220, condition determination can be made robustly regardless of patient position. Further, a trend or progression is determined to provide an indication of whether the patient is improving or worsening. The example apparatus 200 provides a relative measurement or ratio that is more robust to patient position inconsistencies (e.g., a ratio of affected area to total lung area, etc.), for example. For example, lung images can be processed on day and day 2 and leverage AI deep learning and/or other technology to segment the image and annotate to identify an affected part of the lung versus the entire cavity, compute the ratio, and show a worsening from a 42% lung collapse on day 1 to a 56% lung collapse on day 2. Thus, an AI model can drive quantification of change and analysis of condition progression over time.

With 2D images, it is difficult, if not impossible, to obtain absolute values (e.g., absolute volume, absolute size, etc.), but relative measurements, provided by the AI classifier 220, provide a direction of change (e.g., positive, negative, neutral, etc.) and a sense of a magnitude of the change. Thus, an exact measurement is traded for automated evaluation and indication of direction and magnitude of change, for example, and a healthcare practitioner and/or health system knows whether a patient and/or patient population is getting worse or better and to what degree (e.g., much worse or a little better, etc.).

Currently, manual reviews only provide an indication of the presence of a pneumothorax, rather than how much the pneumothorax has changed or how it is being treated. This results in many false alarms. Instead, certain examples can identify whether the condition is getting better or worse and to what degree.

While pneumothorax is used as an example herein, the techniques can apply to a variety of diseases, abnormalities, and/or other conditions such as a hemorrhage, a pulmonary embolism, a lesion or tumor, etc. Certain examples provide a dynamic model or set of dynamic models that can adapt to a variety of changing circumstances, conditions, criteria, etc. For example, changes in lung size depending on whether patient is inhaling or exhaling can be accommodated. A patient's lung filling with fluid (e.g., a plural effusion) can be identified and the model can determine whether the condition is improving or worsening. A tumor can be identified and analyzed to determine whether the tumor is getting bigger or shrinking, for example. One or more AI models can segment, classify, and provide additional information regarding findings.

In certain examples, a condition, such as a pneumothorax, is detected as present or absent, and an exact area of collapse can be localized. An area of the localized contours can be calculated, and that value can be used to determine a relative change in the condition. For example, a relative 2D projection, rather than an actual 3D volume, can be obtained of the pneumothorax and used to determine relative volume, change, and direction of change.

The AI models provide an output that can be post-processed. For example, a mask of a certain size is generated and can be post-processed to calculate pixel area, determine geometry of an area, etc. Thus, the AI model classification output can be post-processed to convert the model output into a measurable physical quantity, even though the model itself may not output a physical quantity, for example.

As discussed above in connection with the example of a pneumothorax, certain examples use a calculated percentage of lung area to describe the size of a lung abnormality. This AI model-driven calculation is robust to different patient sizes, patient positions, etc. The calculation reduces reader subjectivity in determining disease severity. The calculation allows monitoring of progression/regression/stability of a condition over time that is independent of the reader/radiologist/other practitioner. The AI-driven modeling and classification helps to standardize a meaning of Small/Moderate/Large, Mild/Moderate/Severe, or other classification with respect to a particular issue/condition, for example.

Thus, patients in a critical care setting will frequently receive daily chest x-rays to monitor the progression or improvement of lung conditions such as plural effusion (fluid around the lung), consolidation (pneumonia), pneumothorax (lung collapse), etc. Quantifying lung disease or abnormalities within chest radiography historically has been a laborious task, and inaccurate methods of drawing linear measurements or regions of interest are subjected to magnification errors and other inaccuracies, resulting in errors in diagnosis, treatment, prediction, computer-aided detection, etc. As a result, radiologists would conduct one or more subjective methods: size description based on visual impression: trace, small, moderate, large; severity description based on visual impression: mild, moderate, severe; percentage of lung volume estimation from a visual impression. These methods leave room for error on cases where a finding may be borderline mild/moderate or moderate/severe. For example, Radiologist A on day 1 may label a condition mild, and Radiologist B on day 2 may label the condition moderate, despite the condition being stable without any significant changes. However, it's possible that a subtle patient positioning change caused Radiologist B to believe the condition was progressing when reviewing the prior image from day 1. Such an error may cause the ordering physician, who relies on the radiologist's assessments, to change a treatment plan (e.g., medication change or something more invasive such as needle thoracentesis/aspiration) to the detriment of the patient's health and safety. Certain examples help to prevent this occurrence and provide technical improvements to the AI models and operating processor(s).

Figure 13:
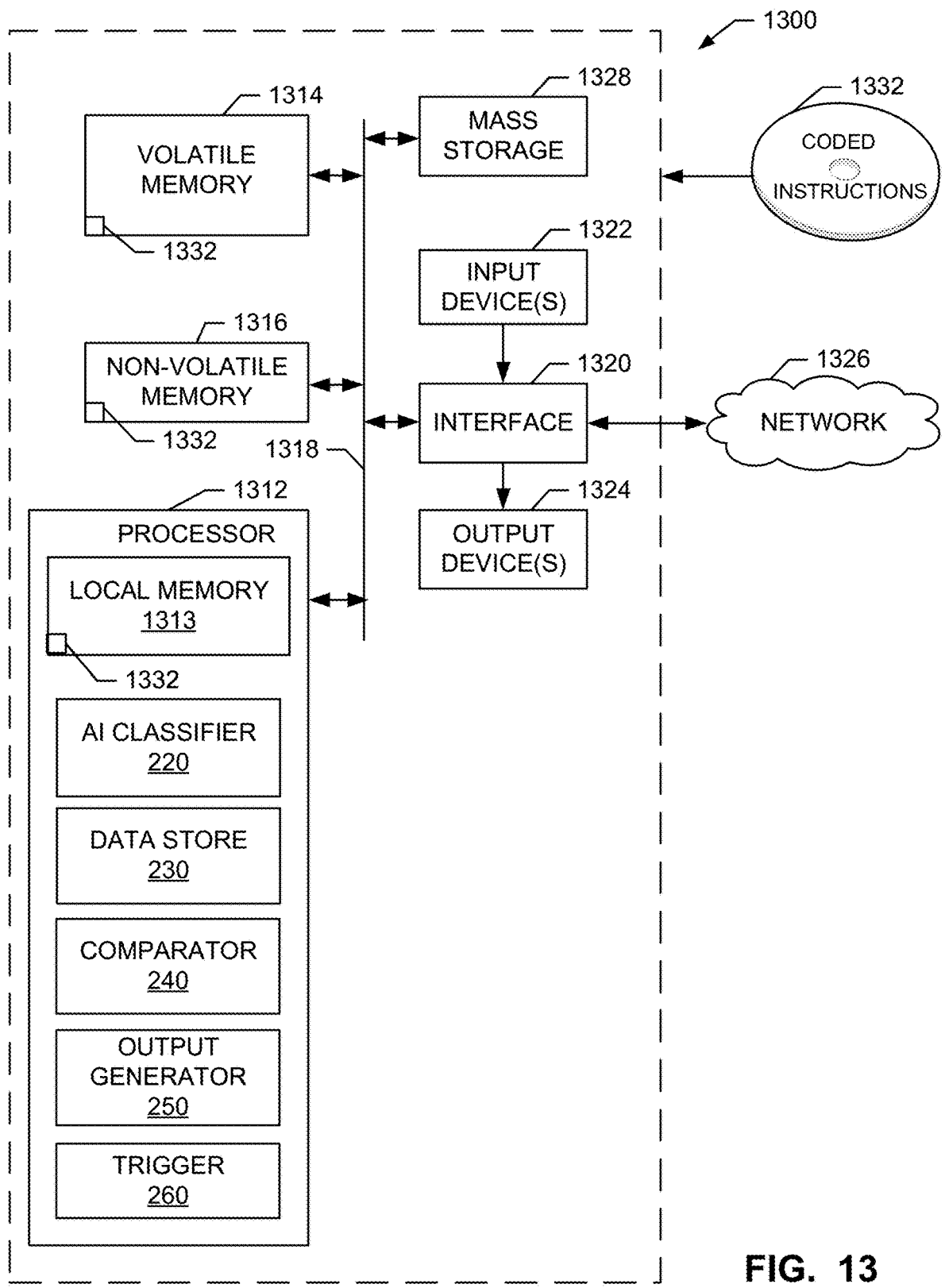
FIG. 13 is a block diagram of a processor platform structured to execute the example machine readable instructions to implement components disclosed and described herein.

FIG. 13 is a block diagram of an example processor platform 1300 structured to executing the instructions of at least FIGS. 11-12 to implement the example components disclosed and described herein. The processor platform 1300 can be, for example, a server, a personal computer, a mobile device (e.g., a cell phone, a smart phone, a tablet such as an iPad™), a personal digital assistant (PDA), an Internet appliance, or any other type of computing device.

The processor platform 1300 of the illustrated example includes a processor 1312. The processor 1312 of the illustrated example is hardware. For example, the processor 1312 can be implemented by integrated circuits, logic circuits, microprocessors or controllers from any desired family or manufacturer.

The processor 1312 of the illustrated example includes a local memory 1313 (e.g., a cache). The example processor 1312 of FIG. 13 executes the instructions of at least FIGS. 11-12 to implement the systems, infrastructure, displays, and associated methods of FIGS. 1-12 such as the example data source 210, AI classifier 220, data store 230, comparator 240, output generator 250, trigger 260, etc. The processor 1312 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 may be implemented by flash memory and/or any other desired type of memory device. Access to the main memory 1314, 1316 is controlled by a clock controller.

The processor platform 1300 of the illustrated example also includes an interface circuit 1320. The interface circuit 1320 may be implemented by any type of interface standard, such as an Ethernet interface, a universal serial bus (USB), and/or a PCI express interface.

In the illustrated example, one or more input devices 1322 are connected to the interface circuit 1320. The input device(s) 1322 permit(s) a user to enter data and commands into the processor 1312. The input device(s) can be implemented by, for example, a sensor, a microphone, a camera (still or video, RGB or depth, etc.), a keyboard, a button, a mouse, a touchscreen, a track-pad, a trackball, isopoint and/or a voice recognition system.

One or more output devices 1324 are also connected to the interface circuit 1320 of the illustrated example. The output devices 1324 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1320 of the illustrated example, thus, typically includes a graphics driver card, a graphics driver chip or a graphics driver processor.

The interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

The coded instructions 1332 of FIG. 13 may be stored in the mass storage device 1328, in the volatile memory 1314, in the non-volatile memory 1316, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques.

Thus, certain examples facilitate image acquisition and analysis at the point of care such as via a portable imaging device at the point of patient imaging. If images should be re-taken, further analysis done right away, and/or other criticality explored sooner, rather than later, the example systems, apparatus, and methods disclosed and described herein can facilitate such action to automate analysis, streamline workflow, and improve patient care.

Certain examples provide a specially-configured imaging apparatus that can acquire images and operate as a decision support tool at the point of care for a critical care team. Certain examples provide an imaging apparatus that functions as a medical device to provide and/or facilitate diagnosis at the point of care to detect radiological findings, etc. The apparatus can trigger a critical alert for a radiologist and/or critical care team to bring immediate attention to the patient. The apparatus enables patient triaging after the patient's exam, such as in a screening environment, wherein negative tests allow the patient to return home, while a positive test would require the patient to be seen by a physician before returning home.

In certain examples, a mobile device and/or cloud product enables a vendor-neutral solution, proving point of care alerts on any digital x-ray system (e.g., fully integrated, upgrade kit, etc.). In certain examples, embedded AI algorithms executing on a mobile imaging system, such as a mobile x-ray machine, etc., provide point of care alerts during and/or in real-time following image acquisition, etc.

By hosting AI on the imaging device, the mobile x-ray system can be used in rural regions without hospital information technology networks, or even on a mobile truck that brings imaging to patient communities, for example. Additionally, if there is long latency to send an image to a server or cloud, AI on the imaging device can instead be executed and generate output back to the imaging device for further action. Rather than having the x-ray technologist moved onto the next patient and the x-ray device no longer at the patient's bedside with the clinical care team, image processing, analysis, and output can occur in real time (or substantially real time given some data transfer/retrieval, processing, and output latency) to provide a relevant notification to the clinical care team while they and the equipment are still with or near the patient. For trauma cases, for example, treatment decisions need to be made fast, and certain examples alleviate the delay found with other clinical decision support tools.

Mobile X-ray systems travel throughout the hospital to the patient bedside (e.g., emergency room, operating room, intensive care unit, etc. Within a hospital, network communication may be unreliable in "dead" zones of the hospital (e.g., basement, rooms with electrical signal interference or blockage, etc.). If the X-ray device relies on building Wi-Fi, for example, to push the image to a server or cloud which is hosting the AI model and then wait to receive the AI output back to the X-ray device, then patient is at risk of not having reliability in critical alerts when needed. Further, if a network or power outage impacts communications, the AI operating on the imaging device can continue to function as a self-contained, mobile processing unit.

Examples of alerts generated for general radiology can include critical alerts (e.g., for mobile x-ray, etc.) such as pneumothorax, tubes and line placement, pleural effusion, lobar collapse, pneumoperitoneum, pneumonia, etc.; screening alerts (e.g., for fixed x-ray, etc.) such as tuberculosis, lung nodules, etc.; quality alerts (e.g., for mobile and/or fixed x-ray, etc.) such as patient positioning, clipped anatomy, inadequate technique, image artifacts, etc.

Thus, certain examples improve accuracy of an artificial intelligence algorithm. Certain examples factor in patient medical information as well as image data to more accurately predict presence of a critical finding, an urgent finding, and/or other issue.

Certain examples evaluate a change in a clinical condition to determine whether the condition is worsening, improving, or staying the same overtime. For example, a critical result from a chest x-ray exam is considered to be a "new or significant progression of pneumothorax", in which the radiologist shall call the ordering practitioner and discuss the findings. Providing an AI algorithm model on an imaging device with prior imaging examines enables the model to determine whether a pneumothorax finding is new or significantly progressed and whether the finding shall be considered critical or not.

Figure 14:
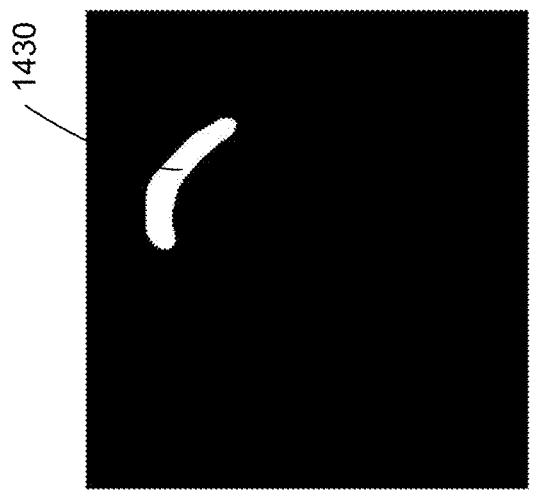
FIGS. 14-15 show example images capture of a patient identifying a pneumothorax, computing a lung ratio, and determining a trend in improvement for the patient condition.
Figure 14:
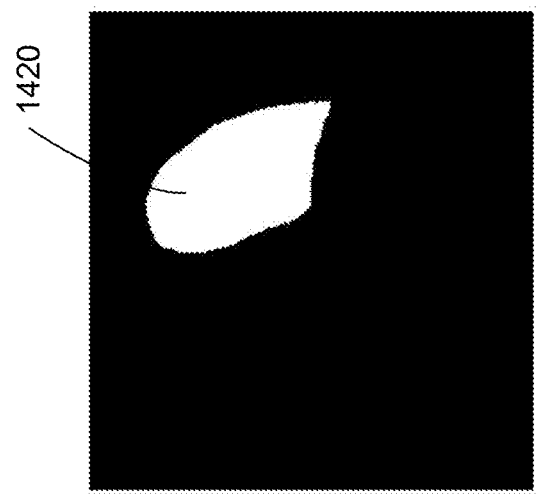
Figure 14:
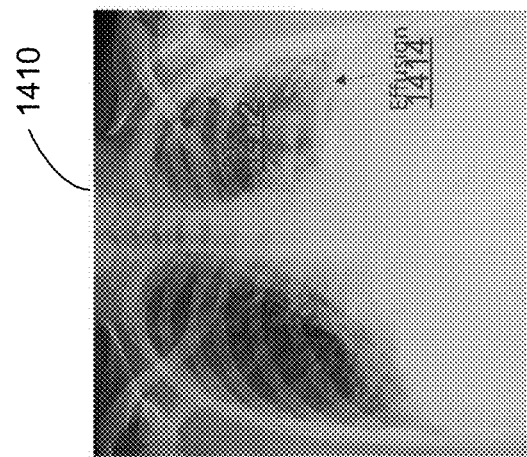

FIG. 14 illustrates an example first image 1410 of a patient with a left lung pneumothorax 1412 and a left lung plural effusion 1414. As shown in the example of FIG. 14, the AI identified the pneumothorax 1412 with a 99% confidence and identified an area through segmentation 1420 of the pneumothorax 1412 as 50,499 pixels. An aerated left lung area includes a segmentation mask 1430 of 240,544 pixels, resulting a ratio of pneumothorax area to aerated left lung area of 21%.

Figure 15:
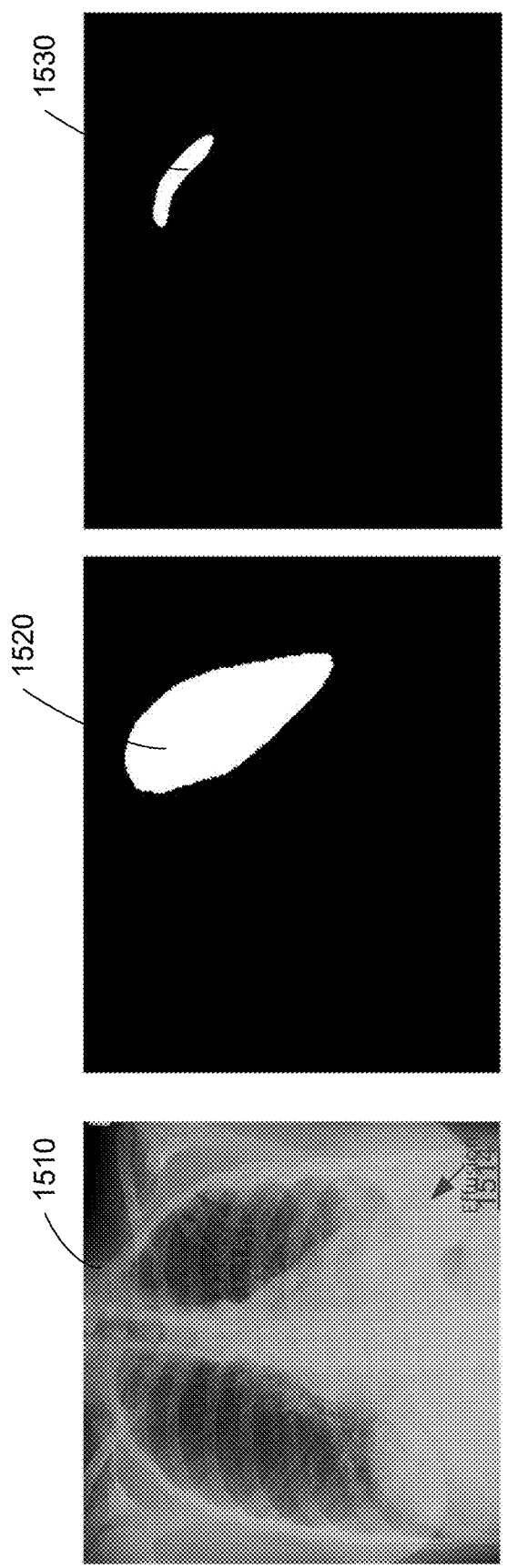

FIG. 15 illustrates an example second image 1510 of the patient with an improving left lung pneumothorax 1512 and left lung plural effusion 1514. As shown in the example of FIG. 15, the AI identified the pneumothorax 1512 with a 41% confidence and identified an area through segmentation 1520 of the pneumothorax 1512 as 26,172 pixels. An aerated left lung area includes a segmentation mask 1530 of 254,905 pixels, resulting a ratio of pneumothorax area to aerated left lung area of 10%, which signals an improvement in the amount of compromised lung region.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An image processing apparatus comprising:
an artificial intelligence classifier including at least one deep learning network model to:
process first image data for a patient from a first time to determine a first classification result indicating a first severity of a condition for the patient; and
process second image data for the patient from a second time to determine a second classification result indicating a second severity of the condition for the patient;
a comparator to compare the first classification result and the second classification result to determine a change and a progression of the condition associated with the change; and
an output generator to trigger an action when the progression corresponds to a worsening of the condition,
wherein the artificial intelligence classifier further includes:
an image segmenter to segment at least one of the first image data or the second image data to obtain a first mask of a region of interest in an organ region in the at least one of the first image data or the second image data and to segment the at least one of the first image data or the second image data to obtain a second mask of the organ region in the at least one of the first image data or the second image data;

a ratio computer to compare the first mask and the second mask to compute a ratio metric to quantify a region of interest in the at least one of the first image data or the second image data; and a condition comparator to generate at least one of the first classification result or the second classification result based on a comparison of the ratio metric to a criterion.

2. The apparatus of claim 1, wherein the action includes at least one of an alert, a recommendation of the action, an order for the action, or an adjustment with respect to the patient to address the condition.

3. The apparatus of claim 1, wherein the artificial intelligence classifier is to be trained with respect to at least three classes of severity for the condition.

4. The apparatus of claim 1, wherein the artificial intelligence classifier further includes a mask combiner to combine the first mask and the second mask and one or more descriptive annotations for the condition comparator.

5. The apparatus of claim 4, wherein the condition includes a pneumothorax, wherein the organ region includes a lung region, and wherein the first mask includes a collapsed region of interest in the lung region.

6. At least one tangible computer-readable storage medium including instructions which, when executed, cause at least one processor to at least:
process, using at least one deep learning network model, first image data for a patient from a first time to determine a first classification result indicating a first severity of a condition for the patient;
process, using the at least one deep learning network model, second image data for the patient from a second time to determine a second classification result indicating a second severity of the condition for the patient;
compare the first classification result and the second classification result to determine a change and a progression of the condition associated with the change; and
trigger an action when the progression corresponds to a worsening of the condition,
wherein processing the first image data and the second image data further includes causing the at least one processor to:
segment at least one of the first image data or the second image data to obtain a first mask of a region of interest in an organ region in the at least one of the first image data or the second image data;
segment the at least one of the first image data or the second image data to obtain a second mask of the organ region in the at least one of the first image data or the second image data;
compare the first mask and the second mask to compute a ratio metric to quantify a region of interest in the at least one of the first image data or the second image data; and
generate at least one of the first classification result or the second classification result based on a comparison of the ratio metric to a criterion.

7. At least one tangible computer-readable storage medium of claim 6, wherein the action includes at least one of an alert, an order, or an adjustment with respect to the patient.

8. At least one tangible computer-readable storage medium of claim 6, wherein the first image data and the second image data are processed using an artificial intelligence classifier, the artificial intelligence classifier including a model to be trained with respect to at least three classes of severity for the condition.

9. At least one tangible computer-readable storage medium of claim 6, wherein the instructions, when executed, further cause the at least one processor to combine the first mask and the second mask and one or more descriptive annotations.

10. At least one tangible computer-readable storage medium of claim 6, wherein the condition includes a pneumothorax, wherein the organ region includes a lung region, and wherein the first mask includes a collapsed region of interest in the lung region.

11. A computer-implemented method comprising:
processing, by executing an instruction using at least one processor and at least one deep learning model, first image data for a patient from a first time to determine a first classification result indicating a first severity of a condition for the patient;
processing, by executing an instruction using at least one processor and the at least one deep learning model, second image data for the patient from a second time to determine a second classification result indicating a second severity of the condition for the patient;
comparing, by executing an instruction using at least one processor, the first classification result and the second classification result to determine a change and a progression of the condition associated with the change; and
triggering, by executing an instruction using at least one processor, an action when the progression corresponds to a worsening of the condition,
wherein processing first image data and second image data further includes:
segmenting at least one of the first image data or the second image data to obtain a first mask of a region of interest in an organ region in the at least one of the first image data or the second image data;
segmenting the at least one of the first image data or the second image data to obtain a second mask of the organ region in the at least one of the first image data or the second image data;
comparing the first mask and the second mask to compute a ratio metric to quantify a region of interest in the at least one of the first image data or the second image data; and
generating at least one of the first classification result or the second classification result based on a comparison of the ratio metric to a criterion.

12. The method of claim 11, wherein the first image data and the second image data are processed using an artificial intelligence classifier, the artificial intelligence classifier including the at least one deep learning network model to be trained with respect to at least three classes of severity for the condition.

13. The method of claim 11, further including combining the first mask and the second mask and one or more descriptive annotations.

14. An image processing apparatus comprising:
an artificial intelligence classifier to:
process first image data for a patient from a first time to determine a first classification result indicating a first severity of a condition for the patient; and process second image data for the patient from a second time to determine a second classification result indicating a second severity of the condition for the patient;

a comparator to compare the first classification result and the second classification result to determine a change and a progression of the condition associated with the change; and an output generator to trigger an action when the progression corresponds to a worsening of the condition, wherein the condition includes a pneumothorax, and wherein a first mask obtained of a lung region of at least one of the first image data or the second image data includes a collapsed region of interest in the lung region.

15. At least one tangible computer-readable storage medium including instructions which, when executed, cause at least one processor to at least:

process first image data for a patient from a first time to determine a first classification result indicating a first severity of a condition for the patient;

process second image data for the patient from a second time to determine a second classification result indicating a second severity of the condition for the patient;

compare the first classification result and the second classification result to determine a change and a progression of the condition associated with the change; and trigger an action when the progression corresponds to a worsening of the condition, wherein the condition includes a pneumothorax, and wherein a first mask obtained of a lung region of at least one of the first image data or the second image data includes a collapsed region of interest in the lung region.

16. A computer-implemented method comprising:

processing, by executing an instruction using at least one processor, first image data for a patient from a first time to determine a first classification result indicating a first severity of a condition for the patient;

processing, by executing an instruction using at least one processor, second image data for the patient from a second time to determine a second classification result indicating a second severity of the condition for the patient;

comparing, by executing an instruction using at least one processor, the first classification result and the second classification result to determine a change and a progression of the condition associated with the change; and triggering, by executing an instruction using at least one processor, an action when the progression corresponds to a worsening of the condition, wherein the condition includes a pneumothorax, and wherein a first mask obtained of a lung region of at least one of the first image data or the second image data includes a collapsed region of interest in the lung region.

* * * * *